(12) United States Patent
Morley et al.

(10) Patent No.: US 10,988,436 B2
(45) Date of Patent: Apr. 27, 2021

(54) CRYSTALLINE FORM OF TRIETHYLENETETRAMINE TETRAHYDROCHLORIDE AND ITS PHARMACEUTICAL USE

(71) Applicant: ORPHALAN S.A., Paris (FR)

(72) Inventors: Timothy James Morley, Harrogate (GB); Ronnie Maxwell Lawrence, Upper Gravenhurst (GB); Naseem Amin, London (GB)

(73) Assignee: Orphalan S.A., Paris (FR)

( * ) Notice: Subject to any disclaimer, the term of this patent is extended or adjusted under 35 U.S.C. 154(b) by 0 days.

(21) Appl. No.: 16/917,266

(22) Filed: Jun. 30, 2020

(65) Prior Publication Data
US 2020/0392068 A1    Dec. 17, 2020

Related U.S. Application Data

(63) Continuation of application No. PCT/EP2019/061441, filed on May 3, 2019.

(30) Foreign Application Priority Data

May 4, 2018 (EP) .................................... 8290048

(51) Int. Cl.
*C07C 211/14* (2006.01)
*C07C 209/84* (2006.01)
*A61K 9/00* (2006.01)

(52) U.S. Cl.
CPC .......... *C07C 211/14* (2013.01); *C07C 209/84* (2013.01); *A61K 9/0053* (2013.01); *C07B 2200/13* (2013.01)

(58) Field of Classification Search
None
See application file for complete search history.

(56) References Cited

U.S. PATENT DOCUMENTS

| 4,187,284 A | 2/1980 | Rolleston et al. |
| 2006/0041170 A1 | 2/2006 | Jonas et al. |

FOREIGN PATENT DOCUMENTS

| CN | 105753719 | 7/2016 |
| CS | 197093 | 4/1980 |
| EP | 1 778 618 | 12/2013 |
| JP | 2001-232495 | 8/2001 |
| JP | 2017-119272 | 7/2017 |
| NZ | 545724 | 11/2007 |
| WO | WO 99/51213 | 10/1999 |
| WO | WO 2003/075910 | 9/2003 |
| WO | WO 2003/077901 | 9/2003 |
| WO | WO 2004/017957 | 3/2004 |
| WO | WO 2006/027705 | 3/2006 |

OTHER PUBLICATIONS

Allen et al., "Tetramine cupruretic agents: A comparison in dogs," *American Journal of Veterinary Research* 48(1):28-30, 1987.

Arciello et al., "Copper depletion increases the mitochondrial-associated SOD1 in neuronal cells," *Biometals* 24(2):269-278, 2011.

Baselt et al., "Comparison of Antidotal Efficacy of Sodium Diethyldithiocarbamate, D-Penicillamine and Triethylenetetramine Upon Acute Toxicity of Nickel Carbonyl in Rats," *Research Communications in Chemical Pathology and Pharmacology* 18(4):677-688, 1977.

Bernal et al., "The Phenomenon of Conglomerate Crystallization. XII. Spontaneous Resolution in Coordination Compounds. IX. The Structure of Racemic [cis-α-Rh(trien)(NO$_2$)$_2$]CL," *Inorganic Chimica Acta* 144:227-232, 1988.

Clay et al., "Noncyclic Reference Ligands for Tetraaza Macrocycles. Synthesis and Thermodynamic Properties of a Series of α,ω-Di-N-methylated Tetraaza Ligands and Their Copper (II) Complexes," *Inorganic Chemistry* 24:3330-3336, 1985.

De Stefano et al., "ΔG° and TΔS° charge relationships for the binding of carboxylic anions by open-chain polyammonium cations," *Journal of the Chemical Society, Faraday Transactions* 94(16):2395-2398, 1998.

"Public summary of opinion on orphan designation, Trientine tetrahydrochloride for the treatment of Wilson's disease," *European Medicines Agency, Science Medicines Health*, EMA/COMP/132991/2015, 4 pages, May 13, 2015.

"Cuprior, Tientine tetrahydrochloride," *European Medicines Agency, Science Medicines Health*, EMA/CHMP/665612/2017, 1 page, Apr. 21, 2017.

Fujito et al., "A Study of Efficient Preparation of Triethylenetetramine Dihydrochloride for the Treatment of Wilson's Disease and Hygroscopy of Its Capsule," *Journal of Pharmaceutical Science and Technology* 50(4):402-408, 1990.

Glerup et al., "Preparation of Chromium(III) Complexes with Two Fluorine Atoms and Four Nitrogen Atoms as Ligators. trans-difluorotetrakis(pyridine)chromium(III) Salts as Initial Materials," *Acta chemical Scandinavica* 24:247-254, 1970.

Henriet et al., "Solid state stability and solubility of triethylenetetramine dihydrochloride," *International Journal of Pharmaceuticals* 511:312-321, 2016.

Hoffman et al., "Synthesis of Bisbasic-Substituted Acridines as Potential Effectors of Nucleic Acids," *Cheminform* 18(9):Abstract 182, 1987.

Ise et al., "Mean Activity Coefficient of Polyelectrolytes. III. Measurements of Hydrochlorides of Polyethylenimine and Its Low Molecular Weight Analogs," *The Journal of Physical Chemistry* 70(7):2400-2405, Jul. 1966.

(Continued)

*Primary Examiner* — Brian J Davis
(74) *Attorney, Agent, or Firm* — Klarquist Sparkman, LLP

(57) ABSTRACT

The present invention describes a new crystalline form of triethylenetetramine tetrachloride which has improved room temperature stability over known forms and over the dichloride salt. The new crystalline form is characterised by having peaks in an XRPD spectrum at 22.9, 25.4, 25.8, 26.6, 34.6 and 35.3±0.1°2θ and Raman shifts 943, 1173, 1527 and 1612±5 cm$^{-1}$. The crystalline form of triethylenetetramine tetrachloride is useful in the treatment of Wilson's disease.

10 Claims, 23 Drawing Sheets

(56) References Cited

OTHER PUBLICATIONS

Ivannikov et al., "Investigation of the influence of high-molecular weight mannich bases with an 8-hydroxyquinoline group on the absorption of radioiodine when it is taken into the digestive tract," *Pharmaceutical Chemistry Journal* 12:178-181, 1978.

Kim et al., "1,16-Dithia-4,7,10,13-tetraazacyclooctadecane and Its Derivatives," *Journal of the Korean Chemical Society* 42(4):458-461, 1998.

Larkworthy et al., "Chromium(II) Chemistry. Part 12. Further Examples of Ferromagnetic Chlorochromates(II)," *Journal of the Chemical Society, Dalton Transactions* 10:1236-1240, 1978.

May et al., "Preparation and characterization of $6^A$-polyamine-mono-substituted β-cyclodextrins," *Journal of the Chemical Society, Perkins Transactions* 1(21):3157-3160, 1997.

Messori et al., "Au$_2$trien: a dinuclear gold (III) complex with unprecedented structural features," *Chemical Communications* 6:612-613, Mar. 2002.

Okubo et al., "Single-Ion Activity Coefficients of Gegenions in Sodium Polyacrylate," *The Journal of Physical Chemistry* 69(11):3690-3695, Nov. 1965.

Peacock, "322. Polyamines. Part II. The preparation of ββ'-diaminodiethylamine and NN'-bis-(β-aminoethyl)ethylenediamine," *Journal of the Chemical Society*, pp. 1518-1520, 1936.

Sakurai et al., "Apparent Molal Volumes of Polyethylenimine Hydrochloride and Its Oligomers in Dilute Aqueous Solution," *Chemistry Letters* 1(5):355-360, 1972.

Seitz et al., "Formation of Hexagonal columnar Mesophases by Linear and Branched Oligo- and Polyamides," *Macromolecules* 29:6560-6574, 1996.

Skruber et al., "Synthesis and Bioelevation of Macrocycle-Polyamine Conjugates as Cell Migration Inhibitors," *Journal of Medicinal Chemistry* 60(20):8606-8619, 2017.

Stefankiewicz et al., "Template-directed synthesis of multi-component organic cages in water," *Chemical Science* 3:2326-2329, 2012.

Thomson et al., "A Chain Model for Polyelectrolytes. IX. The Effects of Chain Length and Charge on the Friction Constant," *Journal of the American Chemical Society* 85(17):2537-2544, 1963.

Walshe, "Copper Chelation in Patients with Wilson's Disease," *Quarterly Journal of Medicine, New Series, XLII* 167:441-452, 1973.

Dauphin et al., "Validated, Stability-Indicated Quantitative Purity Test for Triethylenetetramine Tetrachlorhydrate by Automated Multiple Development," *Journal of Chromatographic Science* 45:315-318, Jul. 2007.

Fargher, "Diethylenetriamine and Triethylenetetramine," *Journal of the Chemical Society, Transactions* 117:1351-1356, 1920.

Humphreys et al., "The development of trientine dihydrochloride, 1977-85," *Orphan diseases and orphan drugs*, pp. 53-55, Manchester University Press, 1986.

Laurie et al., "Potentiometric and Spectroscopic Study of the Equilibria in the Aqueous Copper(II)-3.6,-Diazaoctane-1,8-diamine System and an Equilibrium-dialysis Examination of the Ternary System of Human Serum Albumin-Copper(II)-3,6-Diazaoctane-1,8-diamine," *Journal of the Chemical Society, Dalton Transactions* 19:1822-1827, 1977.

Purchase, "The purification of triethylenetetramine and its dihydrochloride for the treatment of Wilson's disease," *Journal of Chemical Research* 4:233-235, Apr. 2005.

Purchase, "The treatment of Wilson's disease, a rare genetic disorder of copper metabolism," *Science Progress* 96(1):19-32, 2013.

Purchase, "The production of pharmaceutical grade trientine dihydrochloride for the treatment of Wilson's disease: a personal account," *Wilson Disease Support Group—UK Newsletter*, pp. 12-14, 2016.

Roberts, "Trientine for Wilson Disease: Contemporary Issues," *Wilson Disease—Pathogenesis, Molecular Mechanisms, Diagnosis, Treatment and Monitoring*, Chapter 17, pp. 187-195, Academic Press, 2019, available online May 24, 2019.

Rupp et al., "Oral Chelator Treatment of Wilson Disease: Trientine," *Clinical and Translation—Perspectives on Wilson Disease*, Chapter 35, pp. 365-372, 2019, available online Sep. 21, 2018.

Sacconi et al., "Thermochemical Studies. Part VI. Heats and Entropies of Reaction of Transition-metal Ions with Triethylenetetramine," *Journal of the Chemical Society*, pp. 5115-5120, 1961.

Schilsky, "Wilson Disease: New Insights into Pathogenesis, Diagnosis, and Future Therapy," *Current Gastroenterology Reports* 7(1):26-31, Feb. 2005.

Shoukry et al., "Potentiometric Studies of Binary and Ternary Complexes of Zn(II) with Triethylenetetramine as Primary Ligand and Selected Amino Acids and DNA Units as Secondary Ligands," *Mikrochimica Acta* 127:105-111, 1997.

Walshe, "Management of Penicillamine Nephropathy in Wilson's Disease: A new Chelating Agent," *The Lancet* 1401-1402, Dec. 27, 1969.

EASL Clinical Practice Guidesline: Wilson's disease, *Journal of Hepatology* 56:671-685, 2012.

EPO Communication pursuant to Article 94(3) EPC—EPC Application No. 19724752.1 dated Dec. 15, 2020.

Purchase, First Third Party Observation (EP)-WO 2019/211464 dated Nov. 17, 2020.

Purchase, Second Third Party Observation (EP)-WO 2019/211464 dated Dec. 3, 2020.

Purchase, First Third Party Observation (TW)-WO 2019/211464 dated Nov. 19, 2020.

Purchase, Second Third Party Observation (TW)-WO 2019/211464 dated Nov. 27, 2020.

Purchase, Third Party Observation dated Feb. 3, 2021.

Purchase, Third Party Observation (CA)—WO 2019/211464 dated Dec. 4, 2020 but not published by the Canadian Patent Office until Mar. 9, 2021.

Step 1:

Step 2:

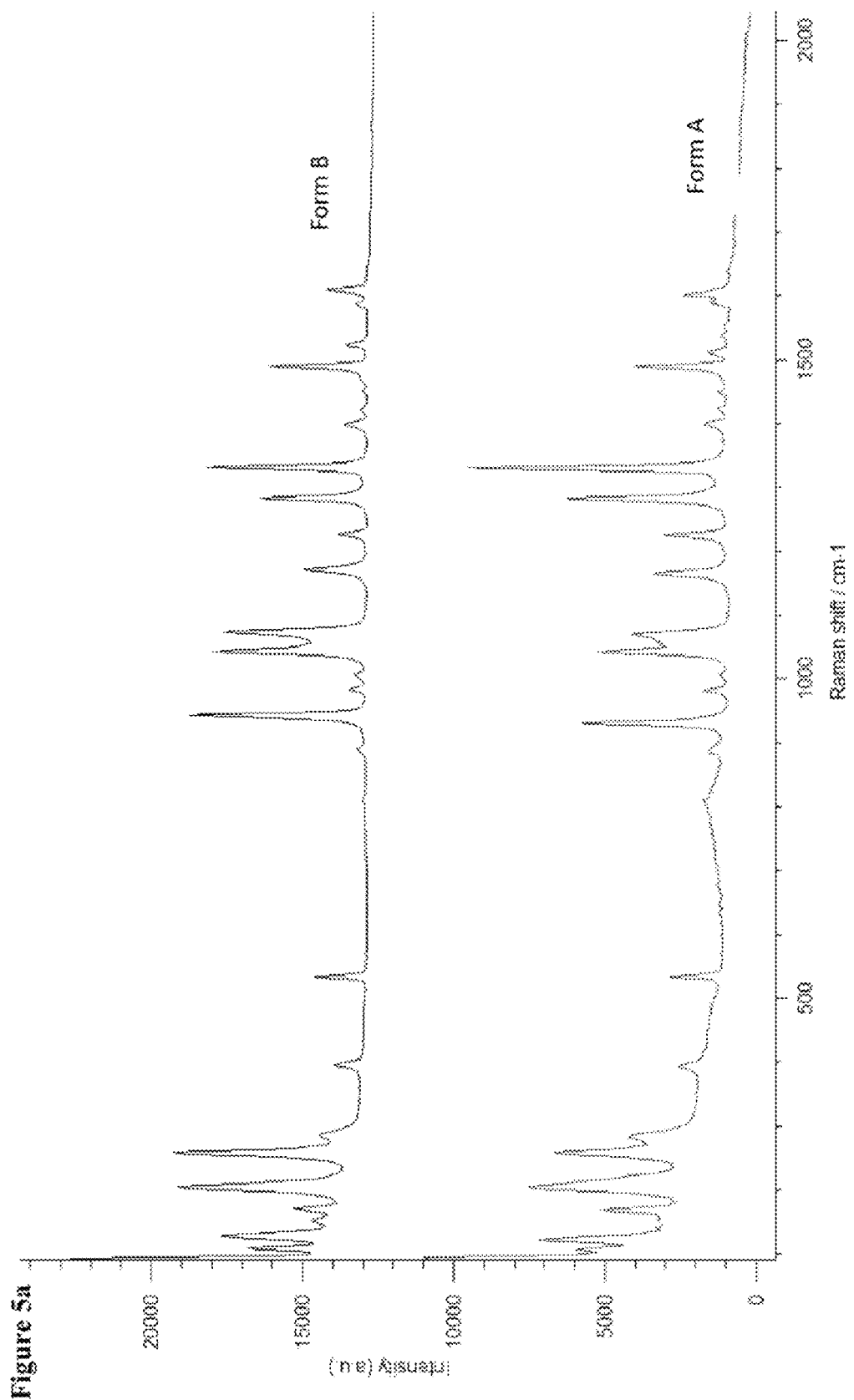

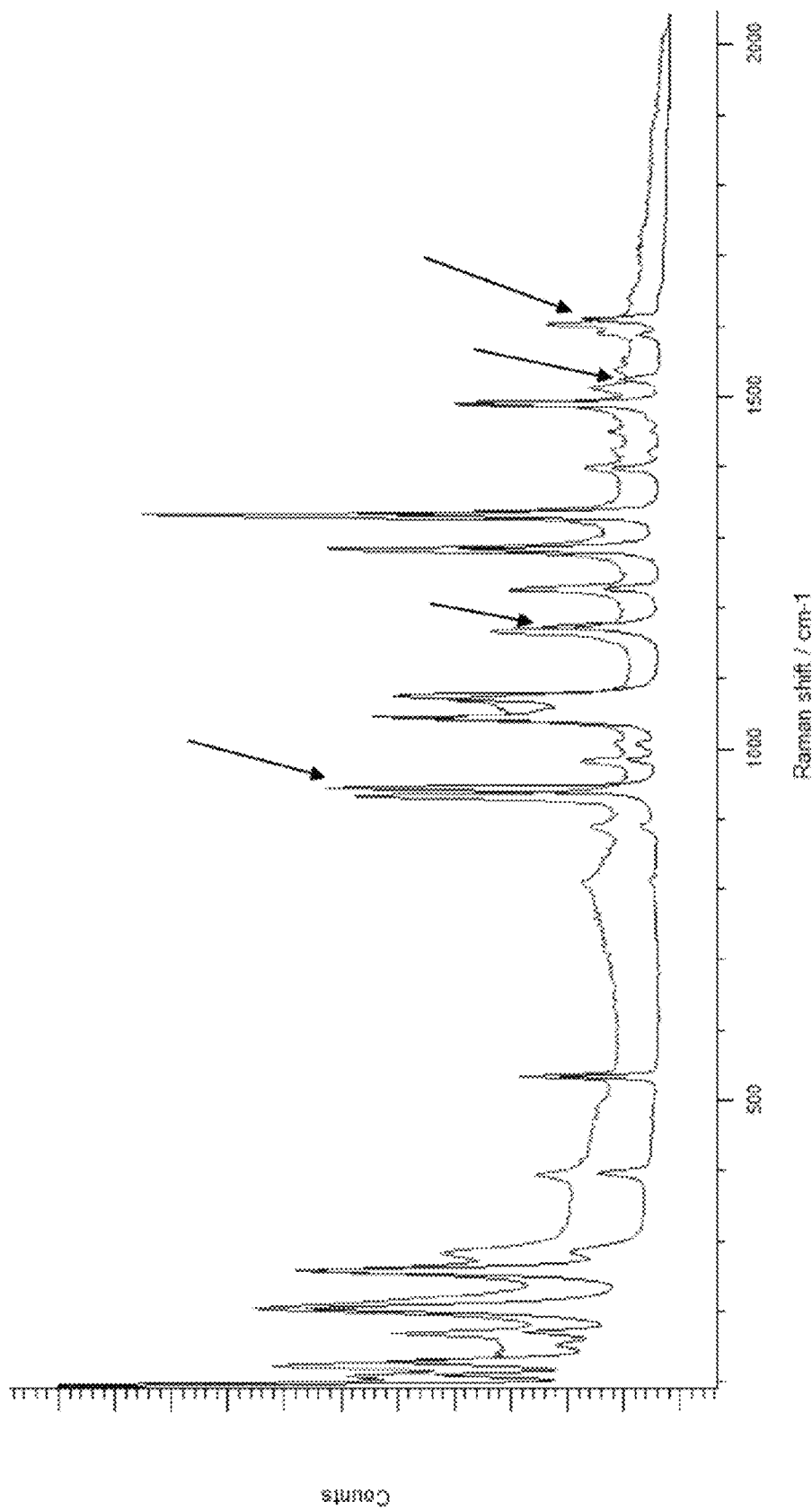

CRYSTALLINE FORM OF TRIETHYLENETETRAMINE TETRAHYDROCHLORIDE AND ITS PHARMACEUTICAL USE

CROSS REFERENCE TO RELATED APPLICATIONS

This application is a continuation of International Application No. PCT/EP2019/061441, filed on May 3, 2019, which in turn claims the benefit of Application No. EP 18290048.0, filed on May 4, 2018. These applications are incorporated herein in their entireties.

FIELD OF THE INVENTION

The invention relates to a crystalline form of triethylenetetramine tetrachloride (TETA.4HCl) and methods of making the crystalline form. The invention further relates to treatment of Wilson's disease using the crystalline triethylenetetramine tetrachloride.

BACKGROUND TO THE INVENTION

Triethylenetetramine, or 1,2-ethanediamine, N, N'-bis(2-aminoethyl) (TETA) has the structure:

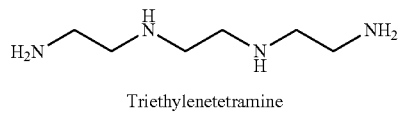

Triethylenetetramine

The dichloride salt (TETA.2HCl) is a polyamine chelator of copper (II). Its copper chelating properties make it useful in the treatment of various conditions, in particular Wilson's disease. Wilson's disease is a genetic disorder caused by a mutation in the Wilson disease protein (ATP7B gene). The condition leads to a build up of copper in the body. The copper chelating ability of TETA.2HCl also led to its consideration for the treatment of numerous conditions such as internal organ damage in diabetes patients, Alzheimer's disease and cancer (Henriet et al, International Journal of Pharmaceutics 511 (2016) 312-321).

However, despite the many years over which TETA.2HCl has been known to be useful for the treatment of Wilson's disease, it has not been a successful treatment. This is, at least in part, because it has proven difficult to provide suitable forms of TETA.2HCl which have sufficient stability at room temperature. It is therefore necessary for patients to store tablets under reduced temperature conditions, an onerous requirement for a treatment which needs to be taken with every meal, for life.

Studies have also shown that variation in humidity can affect the stability of the salt. The salt is very sensitive to water and exists in different polymorphic forms dependent on the humidity levels. High humidity results in instability of the compound. These stability effects lead to challenges in the formulation of a suitable drug for the treatment of patients and the need to store materials under special conditions such as reduced temperature. There is therefore a need for improved treatments for Wilson's disease which can be delivered orally and which are stable under ambient conditions over long periods of time.

EP 1778618 describes synthetic techniques for producing TETA and its salts including the 0.2HCl salt and the 0.4HCl salt. Only the 2HCl salt is said to be useful in the treatment of Wilson's disease.

WO 2006/027705 describes the synthesis of triethylenetetramines, including Form I and Form II triethylenetetramine dihydrochloride. This document does not mention the crystalline forms of triethylenetetramine tetrahydrochloride.

SUMMARY OF THE INVENTION

The present inventors have surprisingly found that a new crystalline form of TETA.4HCl has improved handling properties and room temperature stability. It is therefore more useful for formulation into a drug than either the dichloride or known forms of the tetrachloride salt. Previously known techniques for producing TETA.4HCl (such as anti-solvent crystallisation processes carried out at room temperature, and processes including high temperature drying steps) lead to a crystalline form described herein as Form A. The present inventors, however, have found that by carefully controlling the conditions of manufacture, in particular the temperature and rate of crystallisation, a new crystalline form, known herein as Form B, can be produced. This new form has good handling properties and also good stability and shelf life characteristics and is therefore beneficial in the production of new formulations, for example tablets, for treating Wilson's disease.

The present invention therefore provides a crystalline form of triethylenetetramine tetrachloride having at least one of the following characteristics:
(i) an XRPD pattern having at least two peaks selected from the peaks at 22.9, 25.4, 25.8, 26.6, 34.6 and 35.3±0.1°2θ; and/or
(ii) a Raman spectrum having at least two peaks selected from the peaks at a Raman shift of 943, 1173, 1527 and 1612±5 cm$^{-1}$.

Also provided is a pharmaceutical composition comprising the crystalline form as described herein together with one or more pharmaceutically acceptable carriers or diluents.

Also provided is a method of producing a crystalline form of triethylenetetramine tetrachloride which comprises adding an anti-solvent to an aqueous solution of triethylenetetramine tetrachloride and collecting the crystals obtained, wherein the anti-solvent addition is carried out at a temperature of about 20° C. or below.

Also provided is a crystalline form of triethylenetetramine tetrachloride, or a pharmaceutical composition containing triethylenetetramine tetrachloride, obtainable or obtained by the methods described herein.

Also provided is a crystalline form or pharmaceutical composition as described herein for use in the treatment of the human or animal body by therapy, preferably for use in the prevention or treatment of Wilson's disease.

Also provided is a method for the prevention or treatment of Wilson's disease in a subject in need thereof, which method comprises the administration to the subject of an effective amount of the crystalline form or pharmaceutical composition as described herein.

Also provided is the use of a crystalline form or pharmaceutical composition as described herein in the manufacture of a medicament for the prevention or treatment of Wilson's disease.

Particular aspects of the invention are set out below:
1. A crystalline form of triethylenetetramine tetrachloride having at least one of the following characteristics:
(i) an XRPD pattern having at least two peaks selected from the peaks at 22.9, 25.4, 25.8, 26.6, 34.6 and 35.3±0.1°2θ; and/or
(ii) a Raman spectrum having at least two peaks selected from the peaks at a Raman shift of 943, 1173, 1527 and 1612±5 cm$^{-1}$.
2. A crystalline form according to aspect 1, having an XRPD pattern having at least two peaks selected from the peaks at 22.9, 25.4, 25.8, 26.6, 34.6 and 35.3±0.1°2θ.
3. A crystalline form according to aspect 1 or aspect 2, having an XRPD pattern having at least three peaks selected from the peaks at 22.9, 25.4, 25.8, 26.6, 34.6 and 35.3±0.1°2θ.
4. A crystalline form according to any one of aspects 1 to 3, having an XRPD pattern having peaks at 25.4, 34.6 and 35.3±0.1°2θ.
5. A crystalline form according to any one of aspects 1 to 4, containing no more than 10 wt % of triethylenetetramine tetrachloride Form A having an XRPD pattern having peaks at 25.2 and 35.7±0.10°2θ.
6. A crystalline form according to aspect 5 which contains no more than 5 wt % of triethylenetetramine tetrachloride Form A having an XRPD pattern having peaks at 25.2 and 35.7±0.1°2θ.
7. A crystalline form according to any one of the preceding aspects which consists essentially of triethylenetetramine tetrachloride Form B having:
(i) an XRPD pattern as defined in any one of claims 1 to 4; and/or
(ii) a Raman spectrum having at least two peaks selected from the peaks at a Raman shift of 943, 1173, 1527 and 1612±5 cm$^{-1}$.
8. A pharmaceutical composition comprising a crystalline form according to any one of aspects 1 to 7 and a pharmaceutically acceptable carrier or diluent.
9. A pharmaceutical composition according to aspect 8, which is a solid oral dosage form comprising a crystalline form according to any one of claims 1 to 7 and a pharmaceutically acceptable carrier.
10. A pharmaceutical composition according to aspect 8 or aspect 9, which contains no more than 10 wt %, preferably no more than 5 wt %, more preferably no more than 2 wt % triethylenetetramine tetrachloride Form A having an XRPD pattern having peaks at 25.2 and 35.7±0.1°2θ.
11. A pharmaceutical composition according to aspect 10 which is substantially free of triethylenetetramine tetrachloride Form A having an XRPD pattern having peaks at 25.2 and 35.7±0.1°2θ.
12. A method of producing a crystalline form of triethylenetetramine tetrachloride, which method comprises adding an anti-solvent to an aqueous solution of triethylenetetramine tetrachloride and collecting the crystals obtained, wherein the anti-solvent addition is carried out at a temperature of about 20° C. or below.
13. A method according to aspect 12, wherein the rate of addition of anti-solvent to the solution is no more than 0.5 ml/min per gram of TETA.4HCl dissolved in the aqueous solution.
14. A method according to aspect 12 or aspect 13, which method comprises:
(i) adding anti-solvent to an aqueous solution of TETA.4HCl at temperature T1 over a period of time t1 and/or at a rate of addition R1;
(ii) optionally adding TETA.4HCl seed crystals;
(iii) optionally agitating the resulting mixture at T1 for a further period t1a;
(iv) optionally reducing the temperature to temperature T2 and agitating the mixture for a further period t2; and
(v) collecting the resulting crystals;
wherein T1 is about 20° C. or below; T2 is at least 5° C. lower than T1; t1 is at least 1 hour, R1 is 0.5 ml/min/g or less, t1a is at least 2 hours and t2 is at least 30 minutes.
15. A method according to aspect 14, which method comprises:
(i) adding anti-solvent to an aqueous solution of TETA.4HCl at temperature T1 over a period of time t1 and or at a rate R1;
(ii) optionally adding TETA.4HCl seed crystals;
(iii) optionally agitating the resulting mixture at T1 for a further period t1a;
(iv) reducing the temperature to temperature T2 and agitating the mixture for a further period t2; and
(v) collecting the resulting crystals;
wherein T1 is about 20° C. or below; T2 is about 10° C. or below; t1 is at least 1 hour, R1 is 0.5 ml/min/g or less, t1a is at least 3 hours and t2 is at least 30 minutes.
16. A method according to aspect 15, which method comprises:
(i) adding anti-solvent to an aqueous solution of TETA.4HCl at temperature T1 over a period of time t1 and/or at a rate R1;
(ii) adding TETA.4HCl seed crystals;
(iii) agitating the resulting mixture at T1 for a further period t1a;
(iv) reducing the temperature to temperature T2 and agitating the mixture for a further period t2; and
(v) collecting the resulting crystals;
wherein T1 is about 15° C. or below; T2 is about 5° C. or below; t1 is at least 1 hour, R1 is 0.2 ml/min/g or less, t1a is at least 4 hours and t2 is at least 30 minutes.
17. A method according to any one of aspects 12 to 16 which further comprises drying the collected crystals at a temperature of below about 40° C., preferably below about 30° C.
18. A method according to any one of aspects 12 to 17 wherein the collected crystals are combined with a pharmaceutically acceptable carrier to produce a pharmaceutical composition.
19. A method according to aspect 18, wherein the method further comprises compressing the mixture of crystals and pharmaceutically acceptable carrier to form a tablet and optionally sugar-coating or film-coating the tablet.
20. A crystalline form or pharmaceutical composition obtainable by the method of any one of aspects 12 to 19.
21. A crystalline form or pharmaceutical composition according to any one of the preceding aspects, for use in a method of treating the human or animal body by therapy.
22. A crystalline form or pharmaceutical composition for use according to aspect 21, which is for use in preventing or treating Wilson's disease.

BRIEF DESCRIPTION OF THE FIGURES

FIG. 5a shows the Raman spectra of TETA.4HCl Form A (below) and Form B (above).

FIG. 5b shows the spectra overlaid with Form A in the upper line and Form B the lower line. Form B peaks are highlighted.

FIG. 8a shows the full spectrum 4000-525 $cm^{-1}$. FIG. 8b shows the fingerprint region 1800-525 $cm^{-1}$.

DETAILED DESCRIPTION OF THE INVENTION

Crystalline TETA.4HCl

The crystalline form of triethylenetetramine tetrachloride (TETA.4HCl) which is described herein is known as Form B. This crystalline form can be characterised by one or more of its XRPD spectrum, its Raman spectrum, its melting point, its FTIR spectrum and its DVS behaviour. Details of each of these characteristics of the crystalline form are described below. Typically, the crystalline form of the invention is characterised by its XRPD spectrum and/or its Raman spectrum, most preferably its XRPD spectrum. Thus, the crystalline form of the invention typically has at least one of the following characteristics:
(i) an X-ray powder diffraction (XRPD) pattern having at least two peaks selected from the peaks at 22.9, 25.4, 25.8, 26.6, 34.6 and 35.3±0.1°2θ; and/or
(ii) a Raman spectrum having at least two peaks selected from the peaks at a Raman shift of 943, 1173, 1527 and 1612±5 $cm^{-1}$.

Typically, the crystalline form of TETA.4HCl of the invention has an XRPD pattern having at least two peaks selected from the peaks at 22.9, 25.4, 25.8, 26.6, 34.6 and 35.3±0.1°2θ. Preferably, the XRPD pattern has at least three peaks, more preferably at least four peaks selected from the peaks at 22.9, 25.4, 25.8, 26.6, 34.6 and 35.3±0.1°2θ. More preferably, at least 5 or all of these peaks are observed in the XRPD pattern. More preferably, the crystalline form of TETA.4HCl of the invention has an XRPD pattern having at least two peaks, preferably at least three, four, five or all of the peaks, selected from the peaks at 22.9, 25.4, 25.8, 26.6, 34.6 and 35.3±0.05°2θ It is particularly preferred that the crystalline form of TETA.4HCl has an XRPD pattern having peaks at 25.4, 34.6 and 35.3±0.1°2θ, more preferably at 25.4, 34.6 and 35.3±0.05°2θ.

Typically, the peaks at 25.4 and 35.3±0.1°2θ are the most intense, in particular the peak at 25.4±0.1°2θ. Preferably, the peak at 25.4±0.1°2θ is at least twice as intense as the next most intense peak, more preferably at least three times as intense. Typically, the peak at 35.3±0.1°2θ is at least twice as intense as the next most intense peak.

Figure 4:
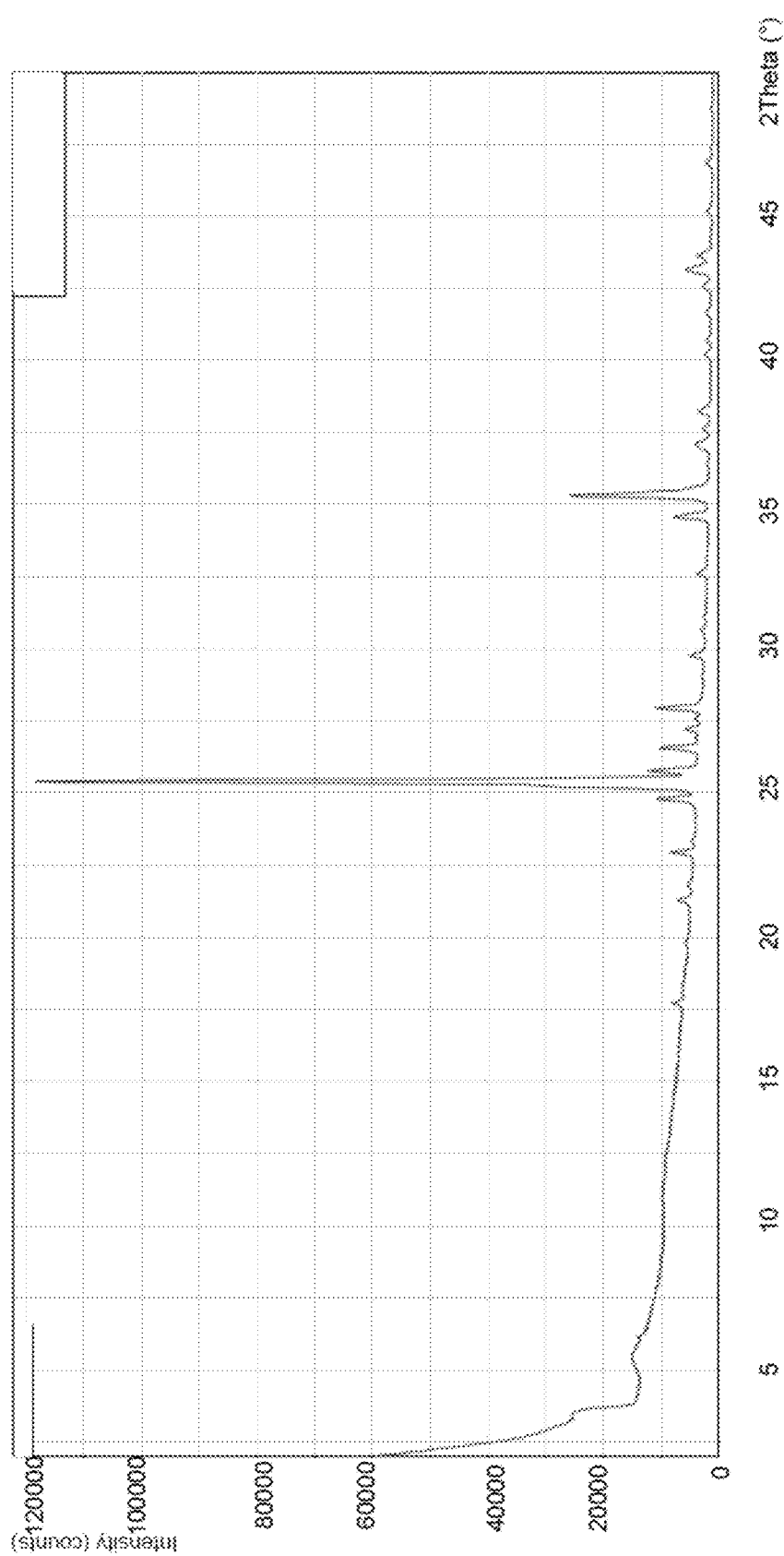
FIG. 4 depicts the X-ray diffraction pattern of TETA.4HCl Form B.

Typically, the XRPD pattern of TETA.4HCl Form B is substantially similar to that depicted in FIG. 4.

XRPD data can be obtained using the PANALYTICAL X'PERT PRO MPD diffractometer. Diffraction data is typically acquired by exposing powder samples to Cu—$K_\alpha$ X-ray radiation, which has a characteristic wavelength (λ) of 1.5418 Å. X-rays were generated from a Cu anode supplied with 40 kV and a current of 40 mA. Further details of operating conditions for obtaining XRPD data are set out in the Examples section herein.

Typically, the crystalline form of TETA.4HCl of the invention has a Raman spectrum having shifts at two or more of 943, 1173, 1527 and 1612±5 $cm^{-1}$. Preferably, the Raman spectrum shows at least two, preferably three, more preferably all four of the peaks at 943, 1173, 1527 and 1612±5 $cm^{-1}$. It is particularly preferred that the crystalline form of TETA.4HCl has a Raman spectrum having shifts at two or more, preferably three, more preferably all four, of 943, 1173, 1527 and 1612±2 $cm^{-1}$. It is particularly preferred that the crystalline form of TETA.4HCl has a Raman spectrum having shifts at 943 and 1173±5 $cm^{-1}$, most preferably 943 and 1173±2 $cm^{-1}$. Typically, the Raman spectrum is similar to that shown in FIG. 5a (upper spectrum).

Raman spectra can, for example, be obtained using a Renishaw RA802 Pharmaceutical Analyser. This can be operated at a laser wavelength of 785 nm. Further operating conditions are set out in the Examples section herein.

The TETA.4HCl Form B crystalline form is storage stable. Thus, typically, the XRPD pattern and/or the Raman spectrum of a sample of the crystalline form of the invention which has been stored at 20° C. for 6 months, preferably 10 months, more preferably 12 months is identical, or substantially identical, to that of the crystalline form of the invention described above. Preferably, at least 90 wt %, more preferably at least 95 wt %, more preferably at least 98 wt % of a sample of the crystalline form of the invention which has been stored at 20° C. for 6 months, preferably 10 months, more preferably 12 months retains the crystalline form, Form B, described herein.

The TETA.4HCl Form B crystalline form is stable in humid environments. Thus, typically, the XRPD pattern and/or the Raman spectrum of a sample of the crystalline form of the invention which has been stored at 40° C. and 75% humidity for 1 month, preferably for four months, more preferably for six months, is identical, or substantially identical, to that of the crystalline form of the invention described above. Preferably, at least 90 wt %, more preferably at least 95 wt %, more preferably at least 98 wt % of a sample of the crystalline form of the invention which has been stored at 40° C. and 75% humidity for 1 month retains the crystalline form, Form B, described herein. Preferably, at least 90 wt %, more preferably at least 95 wt %, more preferably at least 98 wt % of a sample of the crystalline form of the invention which has been stored at 40° C. and 75% humidity for 4 months, preferably for 6 months, retains the crystalline form, Form B, described herein.

Preferably, the storage stability of the crystalline form of the invention is determined by the XRPD pattern. Thus, preferably the XRPD pattern of a sample of the crystalline form of the invention which has been stored at 20° C. for 6 months, preferably 10 months, more preferably 12 months is identical, or substantially identical, to that of the crystalline form of the invention described above. Preferably, at least 90 wt %, more preferably at least 95 wt %, more preferably at least 98 wt % of a sample of the crystalline form of the invention which has been stored at 20° C. for 6 months, preferably 10 months, more preferably 12 months retains an identical or substantially identical XRPD pattern to that of the crystalline form, Form B, described herein. Further, preferably the XRPD pattern of a sample of the crystalline form of the invention which has been stored at 40° C. and 75% humidity for 1 month, preferably 4 months, more preferably 6 months, is identical, or substantially identical, to that of the crystalline form of the invention described above. Preferably, at least 90 wt %, more preferably at least 95 wt %, more preferably at least 98 wt % of a sample of the crystalline form of the invention which has been stored at 40° C. and 75% humidity for 1 month, preferably 4 months, more preferably 6 months, retains an identical or substantially identical XRPD pattern to that of the crystalline form, Form B, described herein.

Alternatively, the storage stability of the crystalline form of the invention is determined by the Raman spectrum. Thus, preferably the Raman spectrum of a sample of the crystalline form of the invention which has been stored at 20° C. for 6 months, preferably 10 months, more preferably 12 months is identical, or substantially identical, to that of the crystalline form of the invention described above. Preferably, at least 90 wt %, more preferably at least 95 wt %, more preferably at least 98 wt % of a sample of the crystalline form of the invention which has been stored at 20° C. for 6 months, preferably 10 months, more preferably 12 months retains an identical or substantially identical XRPD pattern to that of the crystalline form, Form B, described herein. Further, preferably the Raman spectrum of a sample of the crystalline form of the invention which has been stored at 40° C. and 75% humidity for 1 month, preferably 4 months, more preferably 6 months, is identical, or substantially identical, to that of the crystalline form of the invention described above. Preferably, at least 90 wt %, more preferably at least 95 wt %, more preferably at least 98 wt % of a sample of the crystalline form of the invention which has been stored at 40° C. and 75% humidity for 1 month, preferably 4 months, more preferably 6 months, retains an identical or substantially identical Raman spectrum to that of the crystalline form, Form B, described herein.

Figure 7A:
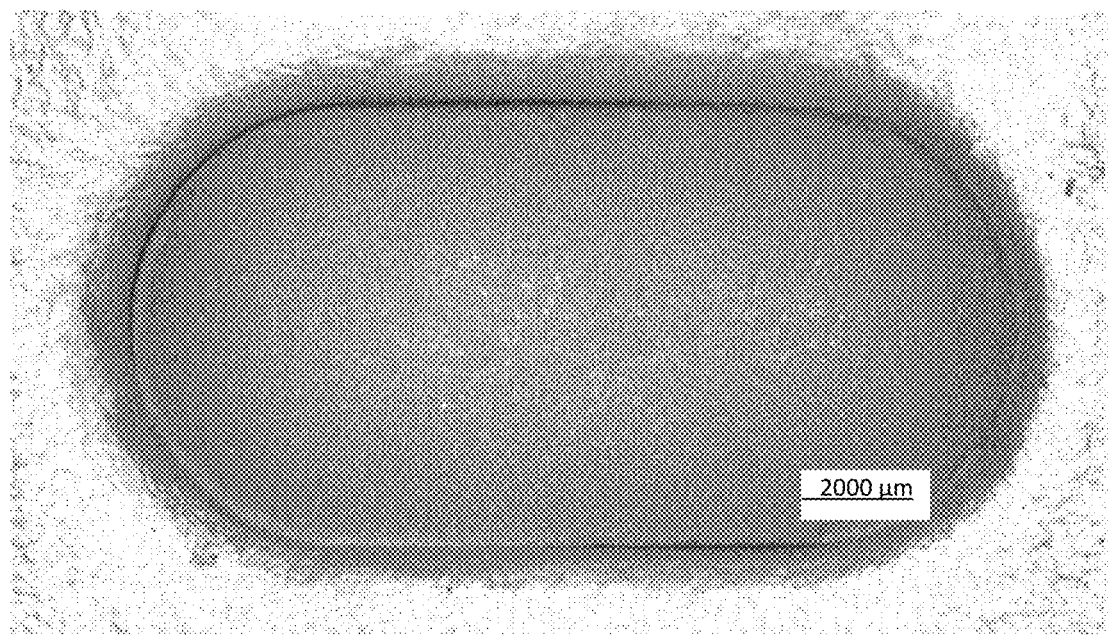
FIG. 7a shows a tablet of TETA.4HCl formed from TETA.4HCl Form A.
Figure 7B:
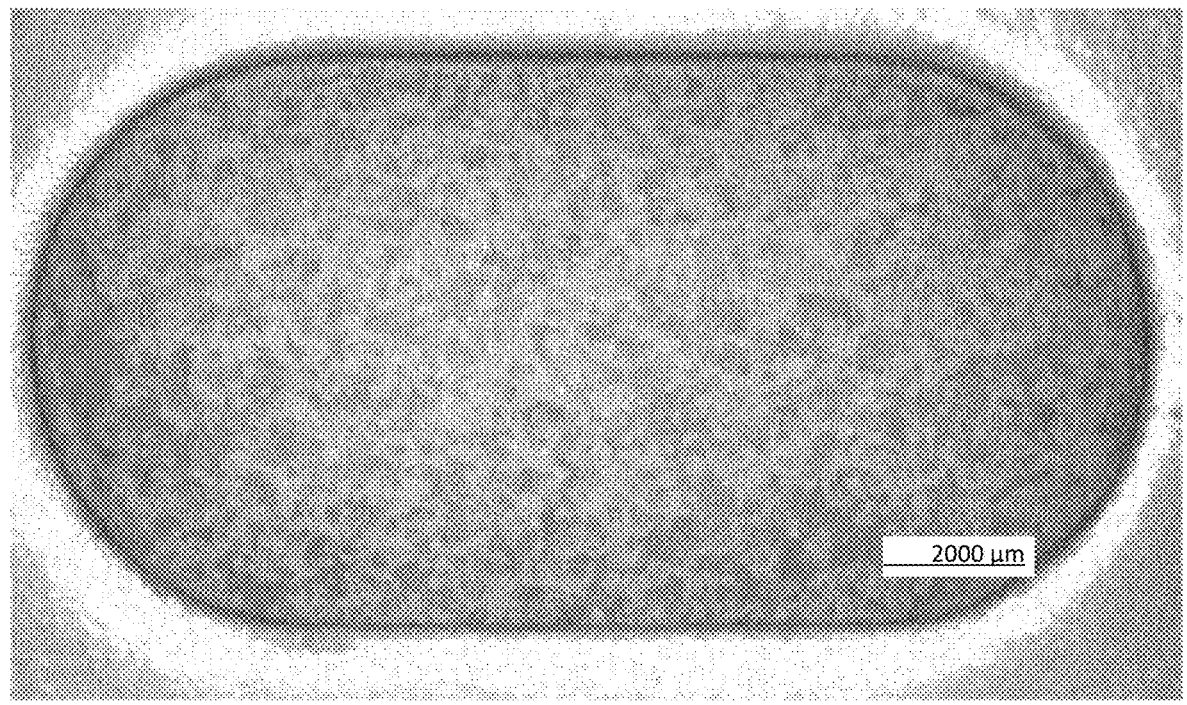
FIG. 7b shows an image of the same tablet after aging.

Particular advantages of the crystalline form of the invention relate to its storage stability. Storage of tablets obtained from Form A TETA.4HCl are observed to have discoloured patches after storage for six months at 40° C. and 75% humidity. A tablet obtained from TETA.4HCl Form A which has been aged is depicted in FIG. 7b. This shows the discolouration of the tablet over time. The present invention and the provision of TETA.4HC Form B, in particular substantially pure TETA.4HCl Form B, is aimed at addressing this issue. Tablets obtained from TETA.4HCl Form B are believed to have a reduced tendency to discolour over time.

The crystalline form of the invention typically has an FTIR spectrum having peaks at two or more, preferably four or more, more preferably five or six or more, most preferably all, of 1475, 1525, 16010, 2380, 2435, 2580, 2830 and 2880±5 cm$^{-1}$. Preferably, the crystalline form of the invention has an FTIR spectrum having peaks at 1525, 2435 and 2675±5 cm$^{-1}$, most preferably at 1526, 2436 and 2674±2 cm$^{-1}$. Preferably, the crystalline form of the invention contains no more than 50 wt %, e.g. no more than 40 wt %, preferably no more than 20 wt %, more preferably no more than 10 wt % of a crystalline form having a peak at 943±2 cm$^{-1}$ in the FTIR spectrum. Most preferably, the crystalline form is substantially free of a crystalline form having a peak at 943±2 cm$^{-1}$.

FTIR spectra are typically FTIR-ATR spectra and can be obtained using a Nicolet iS5 FT-IR spectrometer in ATR diamond mode. Specific conditions suitable for obtaining FTIR spectra are set out in further detail in Example 4.

The crystalline form of the invention typically has a melting temperature of about 260° C., typically about 259° C. as measured by DSC. DSC analysis can be performed as set out in Example 4. For example, analysis can be performed using a Toledo DSC3+ device and providing samples in a 40 μL sealed aluminium pan with the lid punctured before analysis, under nitrogen flush, a 50 mL/min.

Analysis of the crystalline form of the invention by DVS can also be used to distinguish the present crystalline Form B from Form A. The crystalline form of the invention typically shows a weight gain at 90% RH and above of from 50-59%, typically from 54-57%. Typically, after completion of a sorption and desorption cycle (0% to 95% RH) the weight gain of the sample is no more than 10%, preferably no more than 5%. This contrasts with TETA.4HCl Form A which shows a weight gain following sorption/desorption (0-95% RH) of 14-15%.

Typically, the crystalline form of TETA.4HCl according to the invention contains no more than 50 wt %, e.g. no more than 40 wt %, preferably no more than 20 wt % more preferably no more than 10 wt % TETA.4HCl Form A. Preferred crystalline forms of TETA.4HCl according to the invention are substantially free of TETA.4HCl Form A. Substantially free of Form A as used herein means that the crystalline form contains no more than 5 wt % Form A, preferably no more than 2 wt %, more preferably no more than 1 wt % and most preferably no more than 0.5 wt % or no more than 0.1 wt % Form A.

TETA.4HCl Form A is the crystalline form obtained under standard crystallisation conditions, such as those described in Reference Example 3 herein. Form A is characterised by an XRPD pattern having peaks at 25.2 and 35.7±0.1°2θ, typically at 25.2 and 35.7±0.05°2θ. Preferably the XRPD spectrum of Form A also has peaks at 21.8, 26.9 and 28.2 0.1°2θ, typically at 21.8, 26.9 and 28.2±0.05°2θ. In particular Form A is characterised by an XRPD pattern as set out in FIG. 3 ("Profile 1"). Form A may also be characterised by a Raman spectrum having peaks at 933 and/or 1513±5 cm$^{-1}$, typically at 933 and/or 1513±2 cm$^{-1}$. In particular, Form A is characterised by a Raman spectrum having peaks at 933, 1167, 1513 and 1604±5 cm$^{-1}$, typically at 933, 1167, 1513 and 1604±2 cm$^{-1}$. Typically, Form A is characterised by a Raman spectrum as set out in FIG. 5a (lower spectrum) herein.

Preferably, the crystalline form according to the invention contains no more than 50 wt %, e.g. no more than 40 wt %, preferably no more than 20 wt % more preferably no more than 10 wt %, more preferably no more than 5 wt %, no more than 2 wt %, no more than 1 wt % and most preferably no more than 0.5 wt % or no more than 0.1 wt % of a crystalline form of TETA.4HCl having an XRPD pattern having peaks at 25.2 and 35.7±0.1°2θ, or having peaks at 21.8, 25.2, 26.9, 28.2 and 35.7±0.1°2θ.

Preferably, the crystalline form according to the invention contains no more than 50 wt %, e.g. no more than 40 wt %, preferably no more than 20 wt % more preferably no more than 10 wt %, more preferably no more than 5 wt %, no more than 2 wt %, no more than 1 wt % and most preferably no more than 0.5 wt % or no more than 0.1 wt % of a crystalline form of TETA.4HCl having a Raman spectrum having peaks at 933 and/or 1513±5 cm$^{-1}$, typically at 933 and/or 1513±2 cm$^{-1}$, or having peaks at 933, 1167, 1513 and 1604 cm$^{-1}$±5 cm$^{-1}$, typically at 933, 1167, 1513 and 1604±2 cm$^{-1}$.

Preferably, the crystalline form of TETA.4HCl contains at least 90 wt % Form B. More preferably, the crystalline form consists essentially of Form B, i.e. it is substantially pure TETA.4HCl Form B. Where a crystalline form consists essentially of Form B, it typically contains at least 95 wt % TETA.4HCl Form B, more preferably at least 98 wt %, more preferably at least 99 wt %, and most preferably at least 99.5 wt % or 99.9 wt % TETA.4HC Form B, wherein TETA.3HCl Form B is characterised by an XRPD spectrum and/or a Raman spectrum as set out herein, preferably TETA.4HCl Form B is characterised by an XRPD spectrum as set out herein.

The TETA.4HCl crystals described herein are typically provided in dried form. Thus, they typically contain less than 1 wt % water, preferably less than 0.5 wt % water, more preferably less than 0.1 wt % or 0.05 wt % water. Total residual solvent is preferably less than 0.1 wt %, more preferably less than 0.5 wt %.

Methods of Manufacturing Crystalline TETA.4HCl

TETA.4HCl can be produced by techniques known in the art. For example, TETA free base is commercially available and can be converted to the crystalline TETA hydrate and isolated by routine methods. The TETA hydrate can be treated with aqueous HCl to provide the TETA.4HCl salt. Typically, the TETA.4HCl salt is isolated in crude form before recrystallization as the Form B polymorphic form.

TETA.4HCl in crystalline form can be obtained by an anti-solvent crystallisation process, typically from the aqueous solution. Such process involves addition of an anti-solvent to an aqueous solution of TETA.4HCl and collecting the resulting crystals. When carried out under standard crystallisation conditions, for example by crystallising at room temperature or above, and/or by a method including drying at elevated temperature, such methods have been found to lead to a single crystalline form of TETA.4HC, known herein as Form A. Form A crystals were obtained even on variation of the solvent system.

Figure 12A:
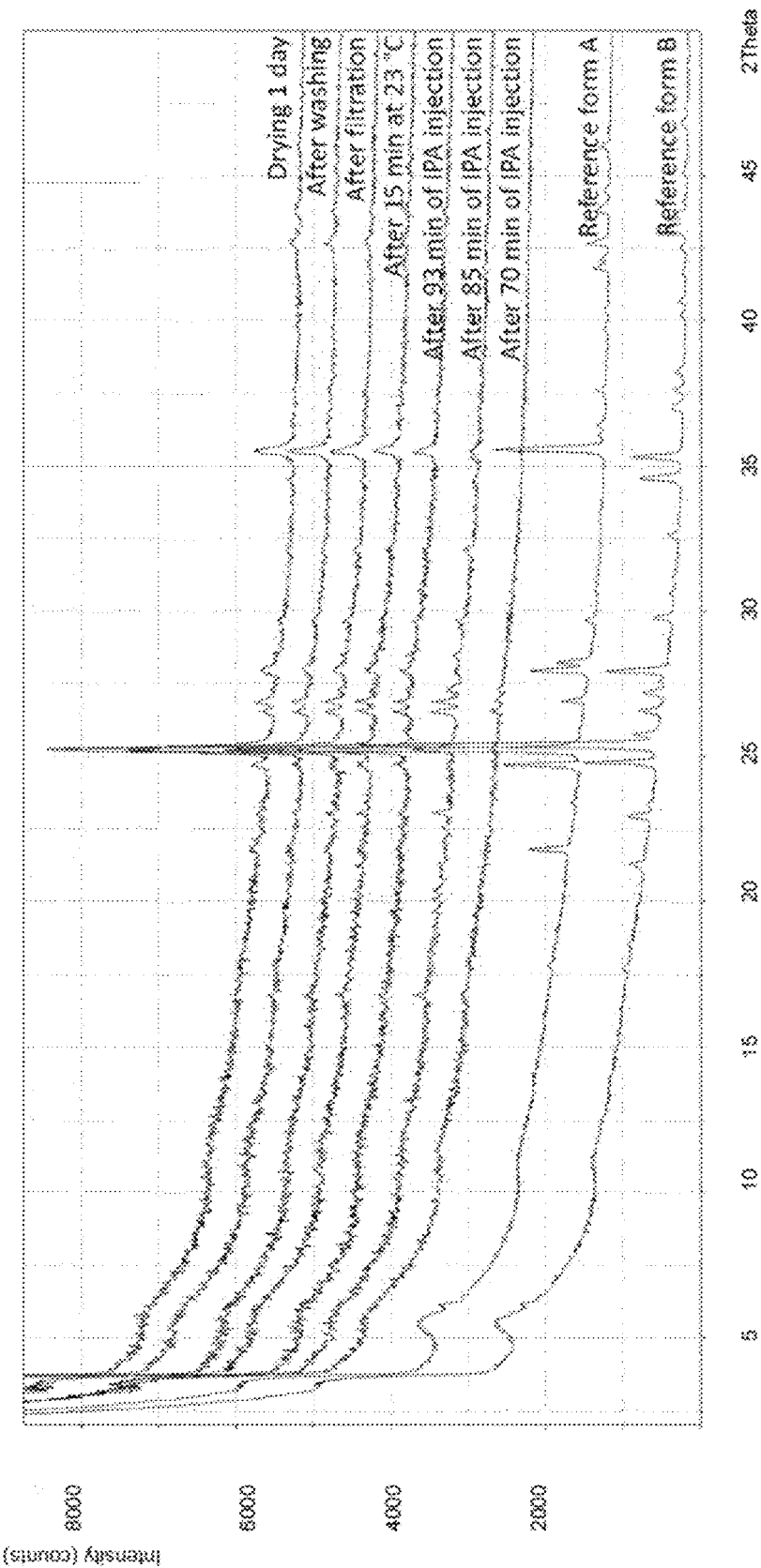
FIGS. 12a to 12c show XRPD spectral analysis of a product produced in accordance with a prior art process.
Figure 12B:
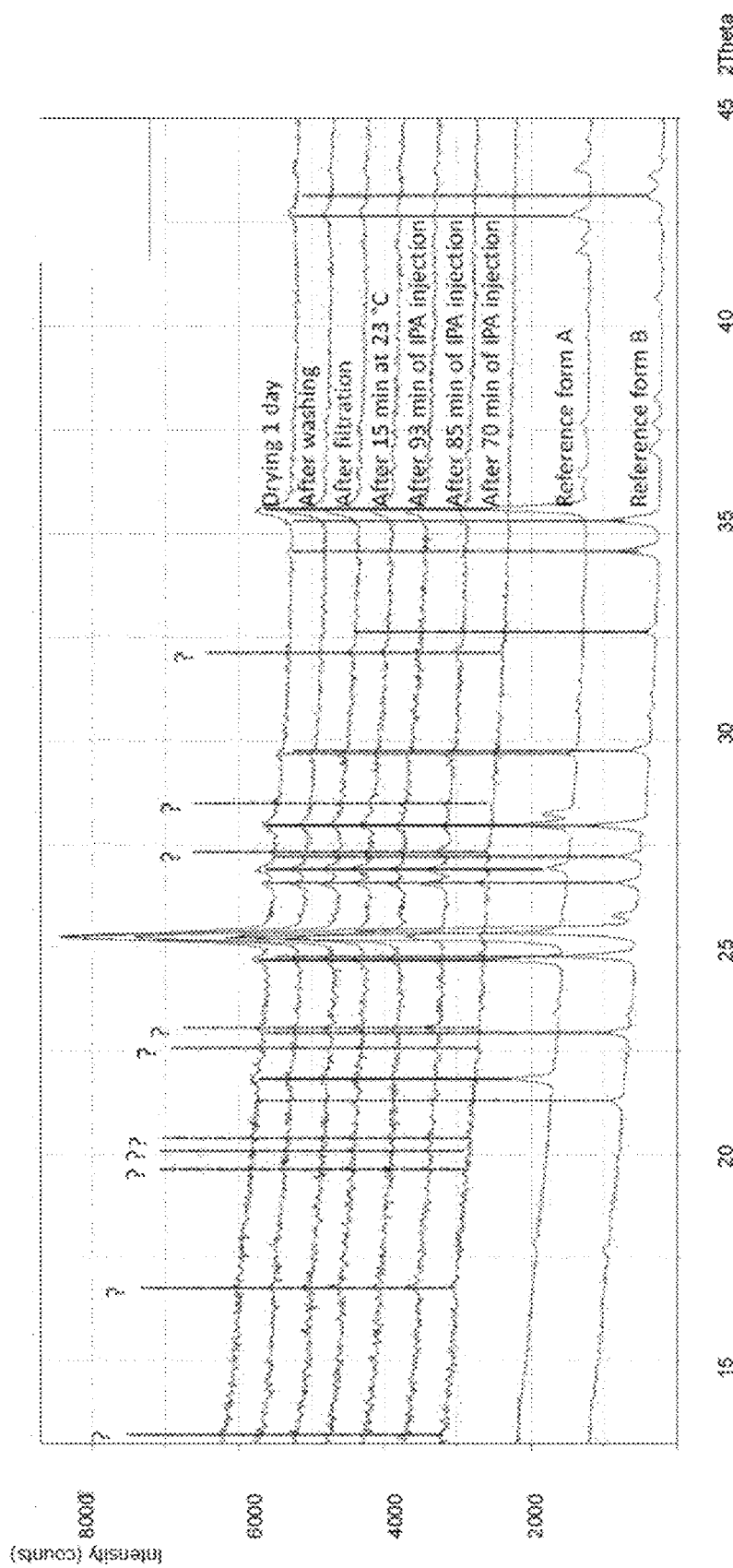
Figure 12C:
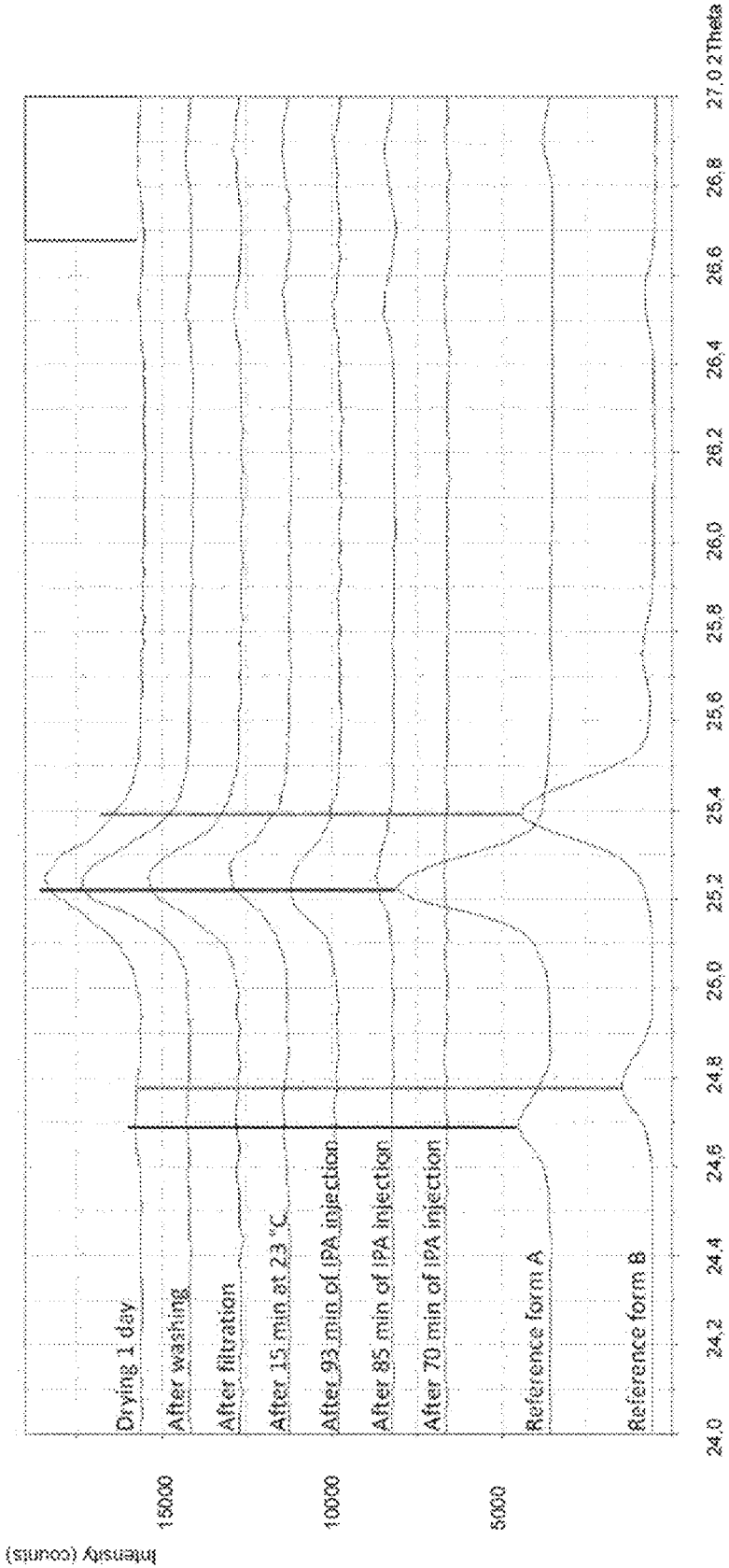

For instance, the present inventors have produced TETA.4HCl using the methods described in WO 2006/027705, and found that these methods lead to production of Form A crystals. The inventors reproduced Example 17 of WO 2006/027705, starting from a mixture of isomers of triethylenetetramine, and using the crystallisation conditions as described in Example 17 of WO 2006/027705. The product was analysed by XRPD and the results are set out in FIGS. 12a to 12c. The product obtained contained the characteristic peaks of TETA.4HCl Form A. However, certain peaks known to be characteristic of TETA.4HC Form B were absent, in particular those at around 35° 2θ and that at 25.4° 2θ, suggesting that the product produced was TETA.4HCl Form A, the form which is known to be produced by standard room temperature crystallisation.

The present inventors have found that, using the same solvent system but varying the crystallisation conditions, in particular the time and temperature of processing, Form B crystals can be obtained.

At temperatures of about 20° C. or below, in particular about 15° C. or below, TETA.4HCl may be produced as Form B. From about 20° C. to 30° C., the crystalline form produced may be dependent on conditions other than simply the temperature of crystallisation. Thus, above about 20° C. further conditions also typically need to be controlled in order to ensure that Form B is produced. In particular, the crystalline form produced may be dependent on the rate of crystallisation. Thus, a slow crystallisation favours formation of Form B, whereas more rapid crystallisation favours Form A. Even at temperatures of from 15-20° C., some Form A crystals may be produced unless crystallisation is carried out slowly. For example where anti-solvent addition is used to form crystals, anti-solvent should preferably be added slowly to the solution in order to ensure that Form B, rather than Form A, is produced.

Typically, the crystalline form of the invention is produced by crystallisation at a temperature of about 20° C. or below, preferably about 15° C. or below, more preferably about 10° C. or below. In one embodiment, preferred temperatures for the crystallisation are 13° C. or below, more preferably from 7-13° C. At temperatures of about 15° C. or below, particularly at 13° C. or below, Form B is the thermodynamically favoured form and crystallisation will generally result in substantially pure Form B.

Preferably, all steps in the crystallisation process are carried out below 30° C., preferably about 20° C. or below, preferably about 15° C. or below, more preferably about 10° C. or below. Where the temperature is above about 15° C., a mixture of Form A and Form B may be produced. Where the temperature is above about 30° C., only Form A will result. To ensure that the product produced is substantially pure Form B, the temperature is preferably kept at about 15° C. or below at all times during crystallisation. At temperatures between about 15° C. and 20° C., Form B crystals can be produced by carrying out crystallisation at a slow rate of anti-solvent addition. In particular, addition of Form B seed crystals combined with slow solvent addition encourages formation of substantially pure Form B. Addition of anti-solvent in a slow and controlled fashion ensures that crystallisation develops from the seed crystal and separate nucleation of Form A does not occur.

Typically, crystallisation is carried out by anti-solvent addition at a rate of 0.5 ml/min or less of anti-solvent added to an aqueous solution of TETA.4HC, per gram of TETA.4HC dissolved in the aqueous solution. Thus, the preferred rate of addition is 0.5 ml anti-solvent, per minute, per gram of TETA.4HCl or less, i.e. 0.5 ml/min/g or less. Preferred rates of anti-solvent addition are 0.2 ml/min/g or less, more preferably about 0.1 ml/min/g or less. Preferred rates of addition are from 0.01 to 0.2 ml/min/g, most preferably from 0.01 to 0.1 ml/min/g.

Thus, to provide substantially pure Form B crystals, crystallisation is preferably carried out at about 15° C. or below and preferably at a rate of addition of 5 ml/min/g or less, more preferably 0.2 ml/min/g or less for example about 0.1 ml/min/g. Most preferably crystallisation is carried out at 13° C. or below, e.g. from 7 to 13° C., and preferably at a rate of addition of less than 0.2 ml/min/g, for example about 0.1 ml/min/g or less.

Seed crystals of TETA.4HCl Form B are preferably added. Seed crystals may be added either before, during or after anti-solvent addition, typically either before or during anti-solvent addition, most preferably before anti-solvent addition. If seed crystals are added either during or after anti-solvent addition, they are preferably added before the formation of crystals are observed.

A preferred method of crystallisation uses TETA.4HC, preferably purified TETA.4HC, as a starting material. The presence of impurities in the starting material can impact the ability to crystallise the desired polymorph. Thus, TETA.4HCl is preferably in isolated form, i.e. it is isolated from any reaction mixture in which it is was produced (and typically purified) before crystallisation to produce Form B is commenced. Further, the crude TETA.4HCl is preferably recrystallized before the process to produce Form B is commenced. This also provides a higher purity starting material and enables Form B crystals reliably to be produced by following the methods as set out herein.

TETA.4HCl is typically dissolved in aqueous solution prior to crystallisation. Typically, the solution comprises from 0.01 to 10 g TETA.4HCl per ml of water. Preferably, the solution comprises from 0.1 to 5 g TETA.4HCl per ml of water, most preferably from 0.6 to 1.2 g TETA.4HCl per ml of water. The volume of anti-solvent used for the recrystallization is typically 0.5 ml or less, per gram of TETA.4HCl dissolved in the aqueous solution. Preferred amounts of anti-solvent are 0.2 ml/g TETA.4HCl or less, more preferably about 0.1 ml/g TETA.4HCl or less. Preferred amounts of anti-solvent are from 0.01 to 0.2 ml/g TETA.4HC, most preferably from 0.01 to 0.1 ml/g TETA.4HCl.

Preferred methods of crystallisation of Form B comprise:
(i) Adding an anti-solvent to an aqueous solution, preferably an agitated aqueous solution, of TETA.4HCl at temperature T1 over a period of time t1 and/or at a rate of addition R1;
(ii) Optionally adding TETA.4HCl seed crystals;
(iii) Optionally agitating the resulting mixture at T1 for a further period t1a;
(iv) Optionally reducing the temperature to temperature T2 and agitating the mixture for a further period t2; and
(v) Collecting the resulting crystals.

T1 is about 20° C. or below, preferably about 15° C. or below, more preferably about 10° C. or below. In order to produce substantially pure Form B, T1 is preferably about 15° C. or below, more preferably about 10° C. or below.

The anti-solvent may be any solvent in which the TETA.4HCl is substantially insoluble. Suitable anti-solvents include ethanol, methanol, acetonitrile, propan-2-ol, acetone and 1,4-dioxane and mixtures thereof. Methanol and ethanol and mixtures thereof are preferred, in particular ethanol.

The solution is typically agitated or mixed during addition, typically by stirring. Further agitation of the mixture, e.g. stirring, may be applied during steps (iii) and (iv).

The crystallisation process is typically carried out over an extended period of time. Thus, t1 is typically at least 1 hour, preferably at least 1.5 hours. The rate of addition of anti-solvent R1 is typically 0.5 ml/min/g or less. Preferred rates R1 are 0.2 ml/min/g or less, more preferably about 0.1 ml/min/g or less, e.g. from 0.01 to 0.2 ml/min/g, most preferably from 0.01 to 0.1 ml/min/g.

If seed crystals are added, these are typically added before, during or after step (i) is carried out. Preferably, seed crystals are added either before step (i) or during the anti-solvent addition of step (i). If seed crystals are added during or after addition of anti-solvent, the mixture is typically stirred for a further prolonged period, t1a, which is preferably at least 2 hours, e.g. at least 3 hours or 4 hours, for example about 5 hours. Preferably, a further stirring period at a lower temperature is also included prior to collection of crystals. This further stirring step is carried out for a period t2 which is preferably at least 30 minutes. The further stirring step is carried out at reduced temperature, T2.

T2 is typically less than T1, preferably at least 5° C., more preferably at least 10° C. less than T. T2 is typically about 10° C. or below, preferably about 5° C. or below, more preferably about 0° C. Increasing the time or rate of crystallisation and reducing the temperature of crystallisation has been found to provide greater purity of Form B. Introducing seed crystals also helps to improve the purity of the Form B crystalline form.

In the method above, typically, T1 is about 20° C. or below; T2 is at least 5° C. lower than T1; t1 is at least 1 hour, R1 is 0.5 ml/min/g or less, t1a is at least 2 hours and t2 is at least 30 minutes. Preferably T1 is about 20° C. or below; T2 is about 10° C. or below; t1 is at least 1 hour, R1 is 0.5 ml/min/g or less, t1a is at least 3 hours and t2 is at least 30 minutes. More preferably T1 is about 15° C. or below; T2 is about 5° C. or below; t1 is at least 1 hour, R1 is 0.2 ml/min/g or less, t1a is at least 4 hours and t2 is at least 30 minutes.

Crystallisation is preferably carried out under inert atmosphere, for example under nitrogen.

Preferred crystallisation methods include at least steps (i), (iv) and (v) above. More preferred methods include steps (i), (iii), (iv) and (v). Most preferred methods include all of steps (i) to (v). Thus, a preferred method of manufacturing TETA.4HCl comprises:
(i) adding anti-solvent to an aqueous solution, typically an agitated aqueous solution, of TETA.4HCl at temperature T1 over a period of time t1 and or at a rate R1;
(ii) optionally adding TETA.4HCl seed crystals;
(iii) optionally agitating the resulting mixture at T1 for a further period t1a;
(iv) reducing the temperature to temperature T2 and agitating the mixture for a further period t2; and
(v) collecting the resulting crystals;
wherein T1 is about 20° C. or below; T2 is about 10° C. or below; t1 is at least 1 hour, R1 is 0.5 ml/min/g or less, t1a is at least 3 hours and t2 is at least 30 minutes.

A further preferred method, which is suitable for producing substantially pure TETA.4HCl Form B comprises:
(i) adding anti-solvent to an aqueous solution, typically an agitated aqueous solution, of TETA.4HCl at temperature T1 over a period of time t1 and/or at a rate R1;
(ii) adding TETA.4HCl seed crystals;
(iii) agitating the resulting mixture at T1 for a further period t1a;
(iv) reducing the temperature to temperature T2 and agitating the mixture for a further period t2; and
(v) collecting the resulting crystals;
wherein T1 is about 15° C. or below; T2 is about 5° C. or below; t1 is at least 1 hour, R1 is 0.2 ml/min/g or less, t1a is at least 4 hours and t2 is at least 30 minutes.

Crystals may be collected by any suitable means as long as the temperature of the collection steps is maintained below about 40° C., preferably below about 30° C. Higher temperature steps carried out before the crystals have been fully dried have been found to lead to Form A crystals only. Most preferably, collection of the crystals is carried out at below about 25° C., for example about 20° C. or below.

Suitable methods for collecting crystals include filtration and centrifuging. Typically, the resulting crystals are then dried, typically at a temperature of below about 40° C., preferably below about 30° C. Crystals may be washed, for example with anti-solvent, prior to drying. Suitable anti-solvents for washing are those mentioned above, in particular methanol or ethanol, most preferably ethanol. Drying is typically vacuum drying, since heating will lead to Form A crystals being produced. Vacuum drying at less than about 40° C. is preferred.

The resulting dried product may be further processed, for example by milling or granulation, if desired. Crystal Form B is substantially stable on milling.

Where relevant, collection and further processing steps such as washing, drying and milling are typically carried out under inert atmosphere, such as under nitrogen.

Pharmaceutical Compositions and Dosage Forms

The pharmaceutical compositions of the invention comprise crystalline TETA.4HC Form B as described herein together with one or more pharmaceutically acceptable carriers or diluents. The pharmaceutical composition may take any suitable form, but is preferably an oral dosage form. For example, the composition may take the form of a tablet, a capsule, a powder, a semisolid, a sustained release formulation, a solution, a suspension or any other appropriate composition. Tablets, capsules and powders, in particular tablets, are preferred.

In alternative embodiments, the compositions are administered parenterally, for example subcutaneously or intravenously.

The pharmaceutical dosage form may be produced by carrying out further processing steps on the crystals produced as described herein. Thus, a composition, typically an oral dosage form, may be produced by (a) obtaining TETA.4HCl Form B, for example using the method described above, (b) optionally milling and/or granulating the crystals obtained, (c) combining the TETA.4HCl Form B with a pharmaceutically acceptable carrier, and (d) optionally mixing the TETA.4HCl Form B and the carrier. Suitable carriers are described further below. Where the oral dosage form is a tablet, the process may further comprise (e) compressing the mixture to form a tablet and optionally sugar-coating or film-coating the tablet. Alternatively, the solid oral dosage form may be a capsule or a powder. In this case, the method of the invention may further comprise (e) packaging the resulting mixture, for example in a capsule. Further standard steps may be included in the process, for example milling, granulating, sugar-coating, or film coating.

The pharmaceutical composition typically comprises up to 85 wt % of TETA.4HCl, for example up to 50 wt % TETA.4HCl. Preferred compositions are sterile and pyrogen free.

Suitable pharmaceutically acceptable carriers for the preparation of oral dosage forms include, for example, solubilising agents, e.g. cyclodextrins or modified cyclodextrins; diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, tragacanth gums, gelatin, syrup, acacia, sorbitol, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in a known manner, for example, by means of mixing, The compositions of the invention typically contain a high proportion of TETA.4HC Form B and a low amount of Form A. Preferably, the pharmaceutical compositions of the invention contain no more than 10 wt % TETA.4HCl Form A. Preferably, the compositions of the invention are substantially free of triethylenetetramine tetrachloride Form A. Substantially free of Form A as used herein means that the composition contains no more than 5 wt %, preferably no more than 2 wt %, more preferably no more than 1 wt %, or 0.5 wt %, and most preferably no more than 0.1 wt % TETA.4HCl Form A.

Medical Uses

A therapeutically effective amount of a compound of the invention is administered to a subject. It will be understood that the specific dose level for any particular subject will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will usually be determined by clinical trial.

A typical daily dose is up to 50 mg per kg of body weight, for example from 0.001 to 50 mg per kg of body weight, according to the age, weight and conditions of the subject to be treated, the type and severity of the disease and the frequency and route of administration. Preferably, daily dosage levels are from 0.05 mg to 2 g, preferably from 0.1 mg to 10 mg. The compound of the invention is typically administered to the patient in a non-toxic amount.

The invention also provides a crystalline form as defined herein or a composition as defined herein for use in a method of treatment of the human or animal body by therapy. In particular the crystalline forms and compositions of the invention are useful in reducing copper levels in a subject and/or reducing the toxic effects of copper retention in a subject. They are therefore useful in the treatment of disorders and diseases associated with raised copper levels. In particular, they are useful in the prevention or treatment of Wilson's disease.

TETA itself is a known treatment for Wilson's disease and diseases and disorders associated with elevated copper levels. After administration of the crystalline form of the invention, the compounds will be dissolved in the in vivo system and the therapeutic effect of the crystalline form can be expected to be the same as known forms of TETA.

The subjects treated according to the present invention may be human or animal subjects, in particular humans or mammals, typically humans.

EXAMPLES

Reference Example 1: Synthesis of TETA.4HCl Crude Form

Figure 1A:
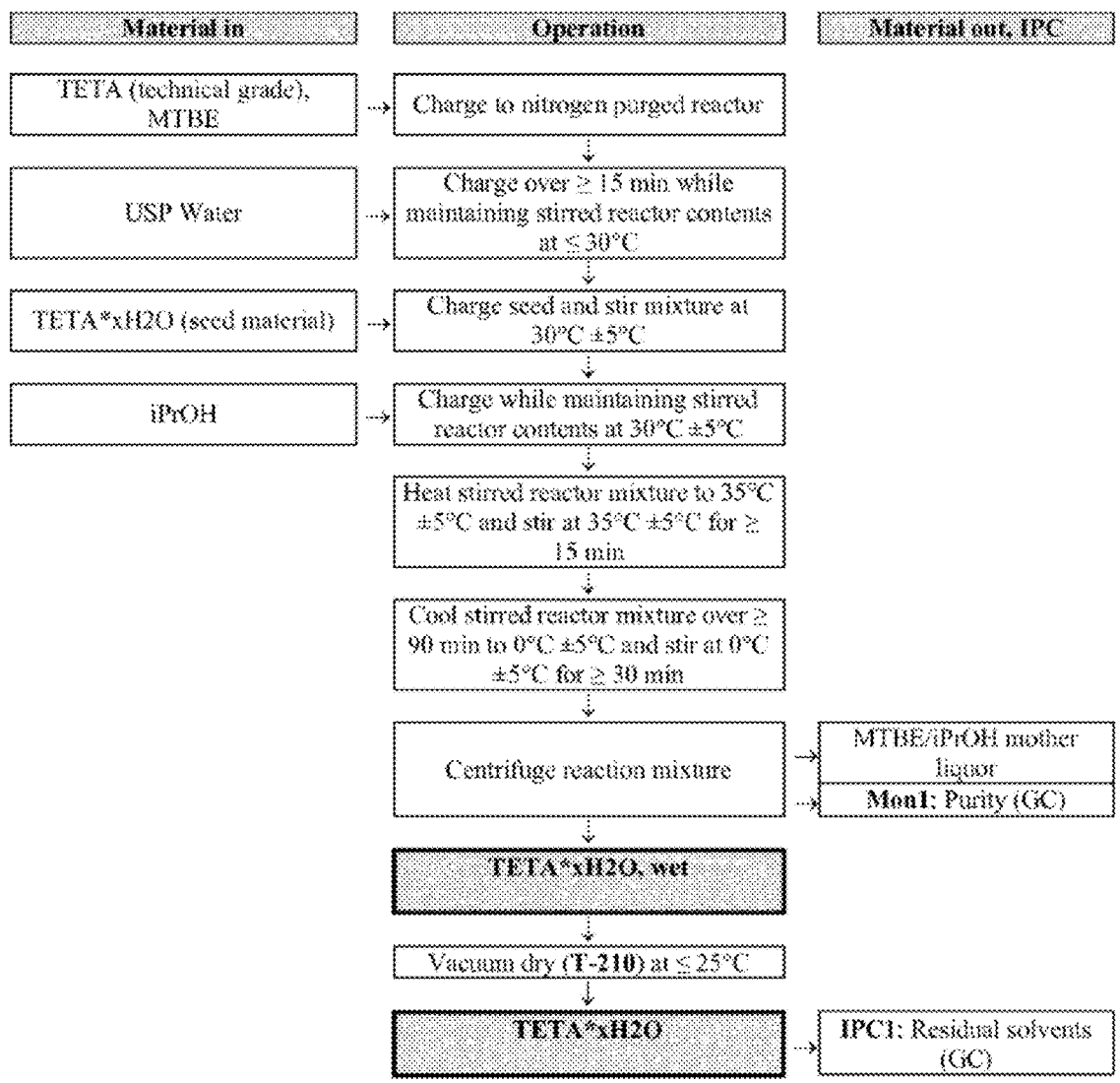
FIGS. 1*a* and 1*b* are flow charts showing a method for producing TETA.4HCl in crude form.
Figure 1B:
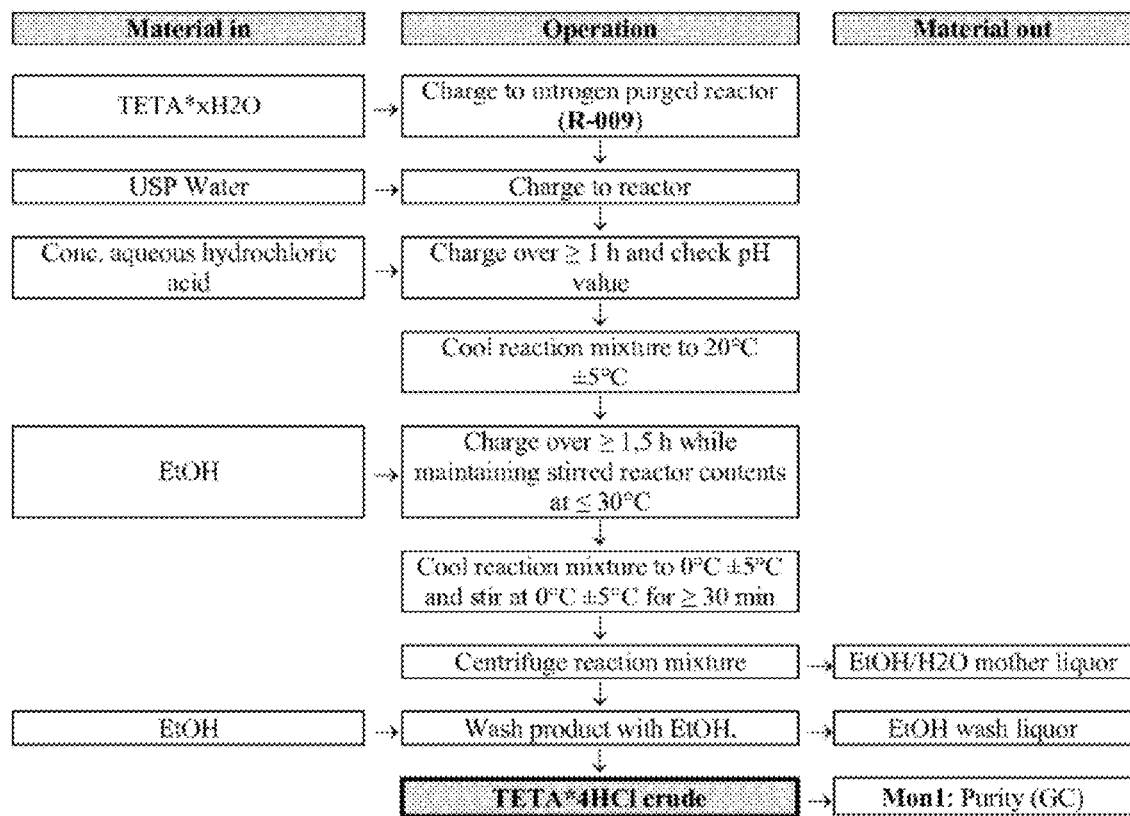

TETA.4HCl in crude form was produced as set out in FIGS. 1a and 1b.

Example 2: Synthesis of TETA.4HCl Form B

Figure 2:
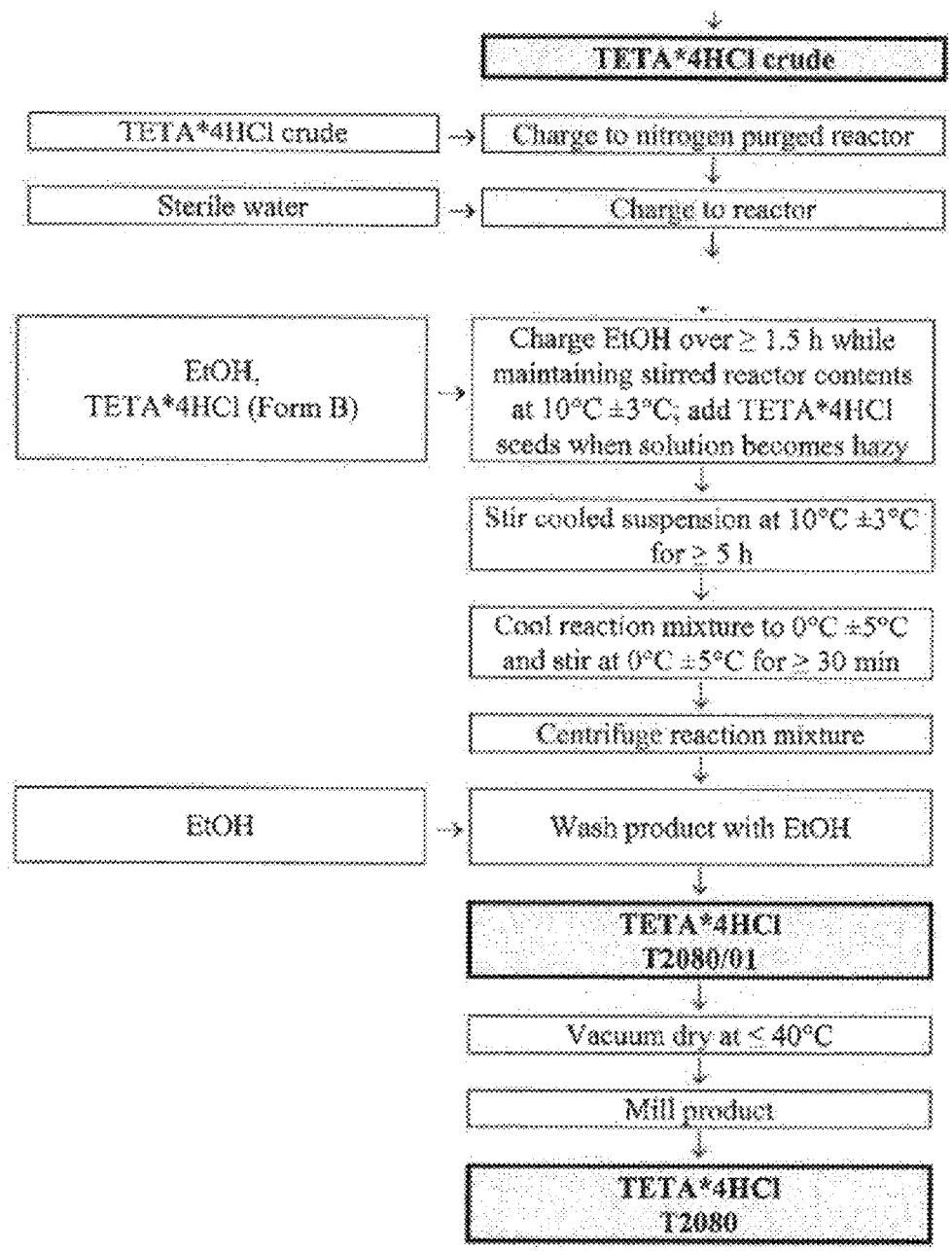
FIG. 2 is a flow chart showing a method for producing TETA.4HCl Form B in substantially pure form.

TETA.4HCl Form B in substantially pure form was produced by following the steps set out in FIG. 2.

Reference Example 3: Synthesis of TETA.4HCl Form A

Crude TETA 4HCl was dissolved under nitrogen in 2 volumes of purified water, and then the solution obtained was clarified by filtration. A reactor was heated at 70° C. (jacket reactor temperature) and when the temperature of the reaction mixture was between 55 and 60° C., 7 volumes of methanol were added to recrystallize the product, at a rate such that the temperature in the mass remained between 55 and 65° C.

After at least 30 minutes of stirring at 65° C. (jacket reactor temperature), the reaction mixture was cooled slowly over a period of at least 2 hours 30 min, while respecting a cooling speed of around 5° C. per 30 min, to obtain a temperature in the mass between 30° C. and 35° C. The suspension was then stirred at least for 1 hour at a temperature in the mass maintained between 30° C. and 35° C.

The product was filtered on an enameled Nutsch filter with 10 μm membrane porosity and washed twice with 1.5 volumes of methanol. Forced filtration was performed after the last wash to dry the product. The product was dried in a vacuum oven at 60° C. for at least 14 hours.

Example 4: Analysis of TETA.4HCl Crystal Forms

X-Ray Powder Diffraction

A few milligrams of the samples obtained in Example 2 and Reference Example 3 above was placed between three polymer foils (Kapton® and polypropylene). Kapton® exhibits a broad peak in the diffractogram with a weak intensity around 2θ=5.5°.

Samples were placed in a PANALYTICAL X'PERT PRO MPD diffractometer configured in transmission mode, and analysed using conditions indicated in Table 1 below. Diffraction data is acquired by exposing powder samples to Cu—K$_\alpha$ X-ray radiation, which has a characteristic wavelength (λ) of 1.5418 Å. X-rays were generated from a Cu anode supplied with 40 kV and a current of 40 mA. The analyses were performed between 2° and 50° (unless stated otherwise). The calibration of the diffractometer was validated before each analysis.

Figure 3:
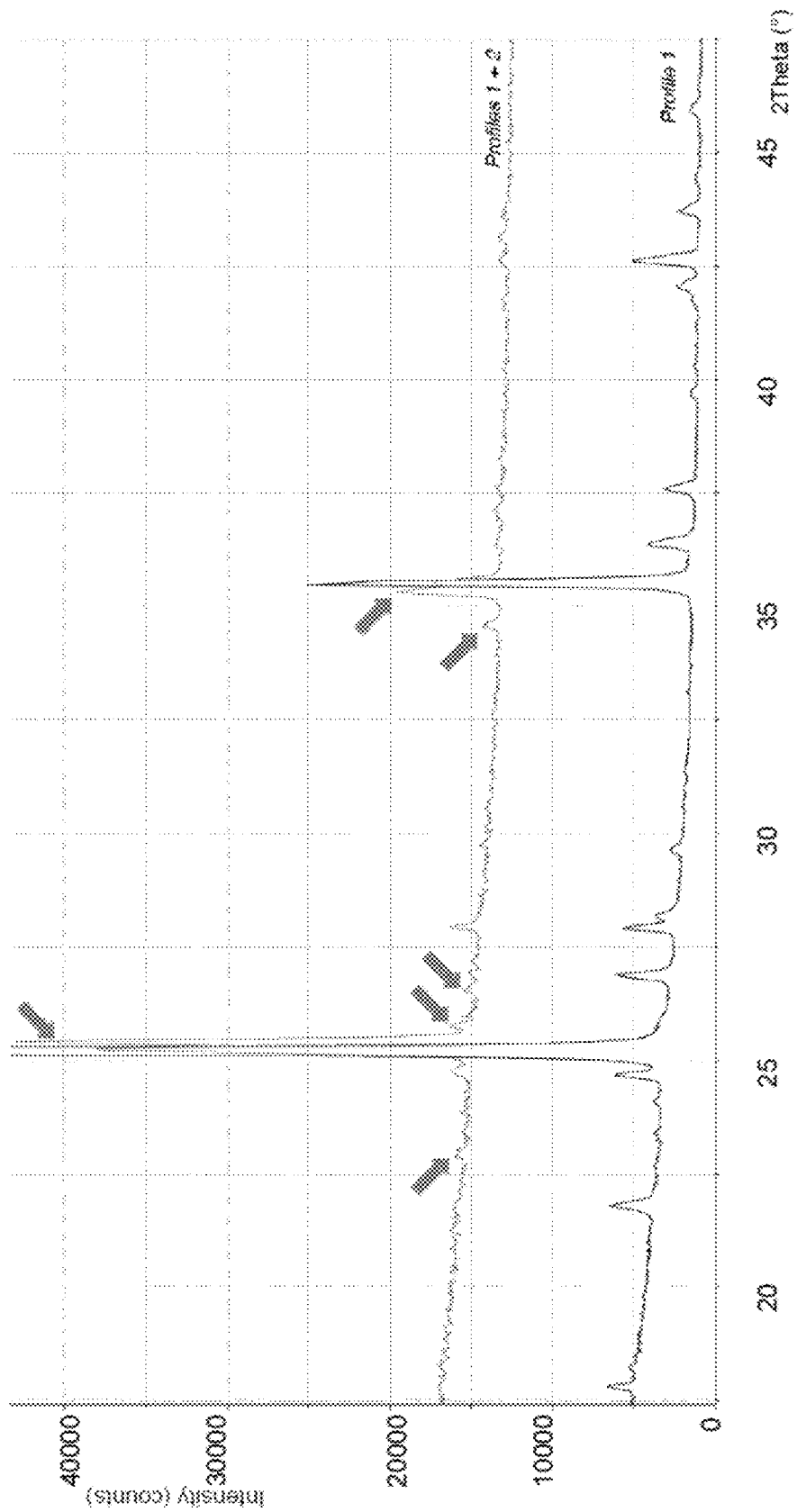
FIG. 3 depicts the X-ray powder diffraction pattern of TETA.4HCl Form A ("Profile 1") and of a mixture of TETA.4HCl Forms A and B ("Profiles 1+2"). Arrows highlight the characteristic peaks of TETA.4HCl Form B.

FIG. 3 shows an XRPD pattern for a mixture of Form A and Form B ("Profiles 1+2") as well as an XRPD pattern for crystals produced in accordance with Reference Example 3 (substantially pure Form A: "Profile 1"). Arrows mark the peaks unique to Form B. FIG. 4 shows an XRPD pattern for crystals produced in accordance with Example 2 (substantially pure Form B).

TABLE 1

| XRPD Analysis Conditions | |
| --- | --- |
| Type | X'Pert Pro MPD Panalytical |
| Serial Number | DY2764 |
| Incident Beam (Transmission Mode) | Radius (mm): 240.0 |
| | X-ray tube: |
| | Name PW3373/10 |
| | Anode Material: Cu |
| | Voltage (kV): 40 |
| | Current (mA): 40 |
| | Focus type: Line (length (mm): 12.0 |
| | width (mm): 0.4 Take-off angle (°): 4.4) |
| | X-ray Mirror: |
| | Name: Inc. Beam Cu W/Si (parabolic MPD) |
| | Crystal (W/Si Graded Parabolic) |
| | Acceptance angle (°): 0.8 |
| | Length (mm): 55.3 |
| | Soller Slit |
| | Soller 0.04 rad. |
| | Opening (rad.): 0.04 |
| | Anti-scatter slit: |
| | AS Slit 1.4 mm (mirror) |
| | Type: Fixed |
| | Height (mm): 1.40 |
| | Divergence slit |
| | Slit Fixed 1/8° |
| | Distance to Sample (mm): 140 |
| | Type: Fixed |
| | Height (mm): 0.19 |

TABLE 1-continued

| XRPD Analysis Conditions | |
| --- | --- |
| Diffracted Beam | Radius (mm): 240.0 |
| | Soller slit |
| | Name: Large Soller 0.04 rad. |
| | Opening (rad.): 0.04 |
| | Detector |
| | Name: PIXcel |
| | Type: RTMS detector |
| | PHD - Lower level (%): 25.5 |
| | PHD - Upper level (%): 70.0 |
| | Mode: Scanning |
| | Active length (°): 3.347 |

Raman Spectroscopy

Samples of Example 2 and Reference Example 3 were analysed by Raman spectroscopy. A Renishaw RA802 Pharmaceutical Analyser was used under the following conditions:

TABLE 2

| Laser wavelength | 785 nm |
| --- | --- |
| Spectral dispersion | 2 cm$^{-1}$/pixel |
| Objective | Hi Mag (×50 - 1 μm capability) |
| Focussing | Automatic (LiveTrack) |
| Acquisition time | 1 s |
| Laser power | 50% |

The spectra are provided in FIGS. 5a and 5b. In FIG. 5b, the lower line represents Example 2 (Form B), whilst the upper line represents Reference Example 3 (Form A). Arrows depict shifts unique to Form B. The Raman spectrum for Example 2 shows bands at 943, 1173, 1527 and 1612 cm$^{-1}$. The Raman spectrum for Reference Example 3 (Form A) shows peaks at 933, 1167, 1513 and 1604 cm$^{-1}$.

FTIR-ATR Analysis

Infrared spectra are measured on a Nicolet iS5 FT-IR spectrometer equipped with an iS7 ATR module, with the parameters set out below:

TABLE 3

| Mode | ATR Diamond |
| --- | --- |
| Resolution | 4 cm$^{-1}$ |
| Number of scans (measurement) | 32 scans |
| Number of scans (background) | 32 scans |
| Spectrum | 4000 cm$^{-1}$ to 525 cm$^{-1}$, in absorbance |

Figure 8A:
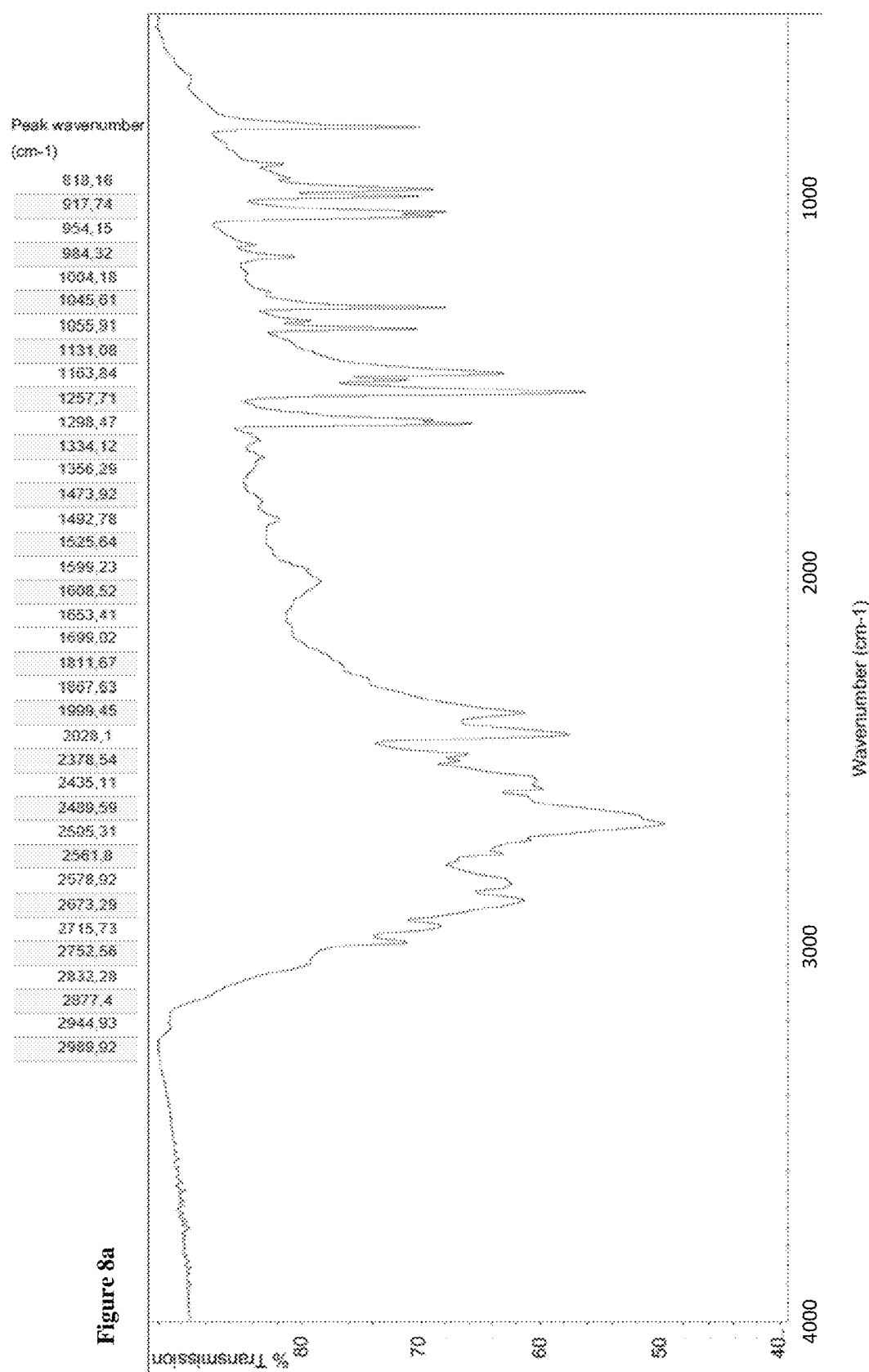
FIGS. 8a and 8b show the FTIR-ATR spectra of TETA.4HCl Form B.
Figure 8B:
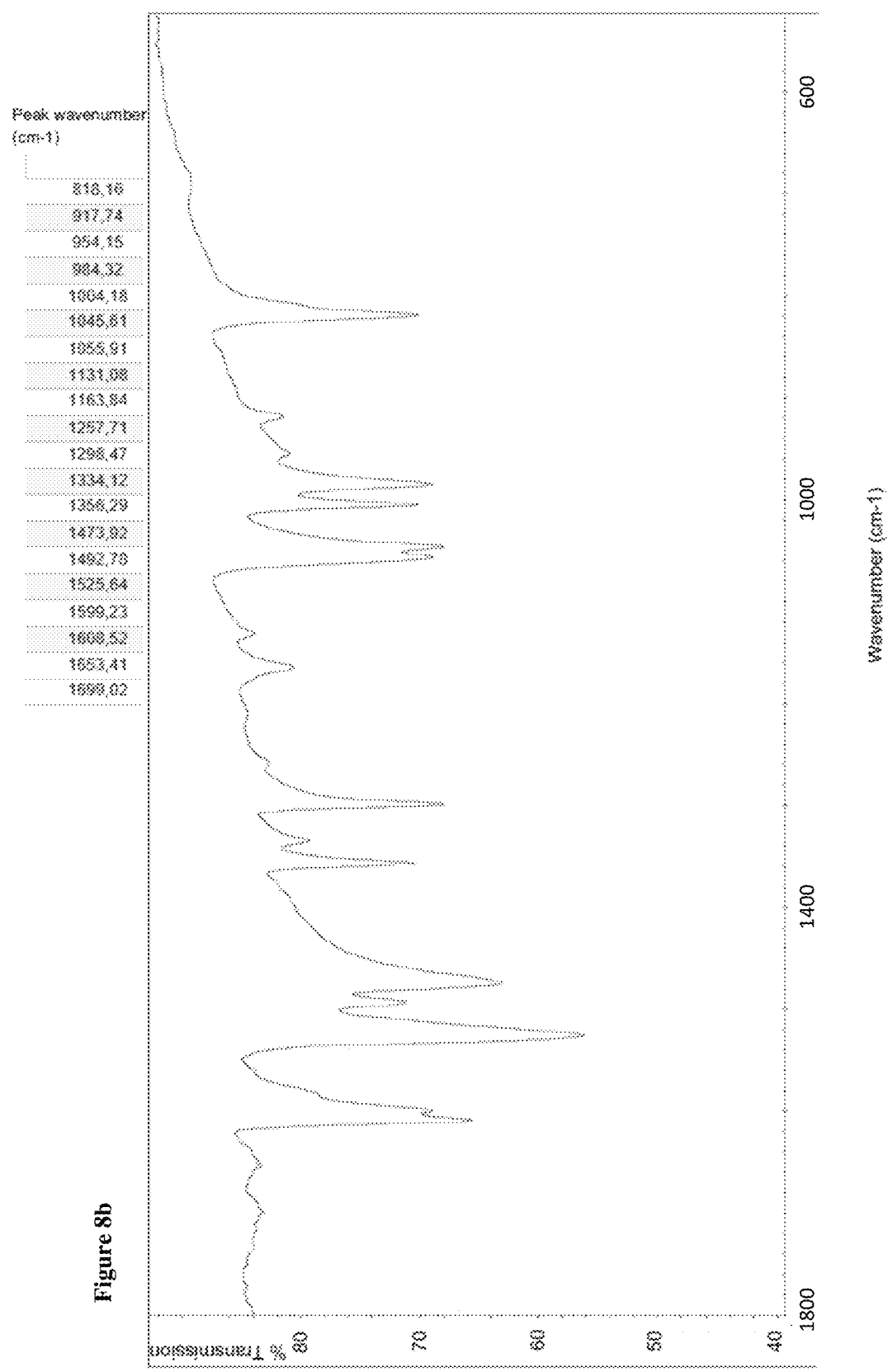

An infra-red spectrum was obtained for Example 2 (Form B). The spectrum is shown in FIGS. 8a and b.

DSC Analysis

DSC analyses were performed using a Mettler Toledo DSC3+(serial number B531255222) in 40 μl sealed aluminium pans with the lid punctured before analysis, under nitrogen flush at 50 mL/min.

TABLE 4

| Sample ID | Example 2 |
| --- | --- |
| Sample weight | 0.360 mg |
| Scanning range | 20° C.-300° C. |
| Scanning rate | 10°/min |

An endothermal event corresponding to the melting of the sample is observed. Onset and peak temperatures are shown in the Table below.

TABLE 5

| T Onset (° C.) | T Peak (° C.) | Enthalpy (J/g) | Comment |
|---|---|---|---|
| 252.1 | 259.2 | 232.1 | Melting |

Onset, peak temperatures and enthalpies

Thermogravimetric Analysis (TGA)

Thermogravimetric analyses were performed using a Pyris 1 TGA analyser (serial number 537N7052501) in sealed aluminium pans, punctured before analysis, under nitrogen flush at 20 mL/min.

TABLE 6

| | |
|---|---|
| Sample ID | Example 2 |
| Sample weight | 5.100 mg |
| Start temperature | 25° C. |
| End temperature | 300° C. |
| Scanning rate | 10° C./min |

The thermogravimetric analysis shows a weight loss starting at 225° C., which increases after 289.5° C. This is likely due to degradation. Weigh loss was 10.24%: 2.64% between 225.0-289.5° C. and 7.60% between 289.5-299.0° C.

Dynamic Vapour Sorption (DVS) Analysis

DVS analyses are performed using an SMS DVS Intrinsic analyser (serial number PF 140088) in open aluminium pans at 25° C. with a nitrogen purge gas at 100 ml/min. The stability criterion was a weight change lower than 0.002% on a 5 minute time frame (with a minimum of 10 min and a maximum of 100 min).

TABLE 7

| | |
|---|---|
| Sample ID | Example 2 |
| Sample weight | 11.2773 mg (initial) |
| | 11.2763 mg (ref. 0% RH) |
| Temperature | 25° C. |
| Relative Humidity program | 1) 40% RH-0% RH |
| | 2) 0% RH-95% RH |
| | 3) 95% RH-0% RH |

Figure 11A:
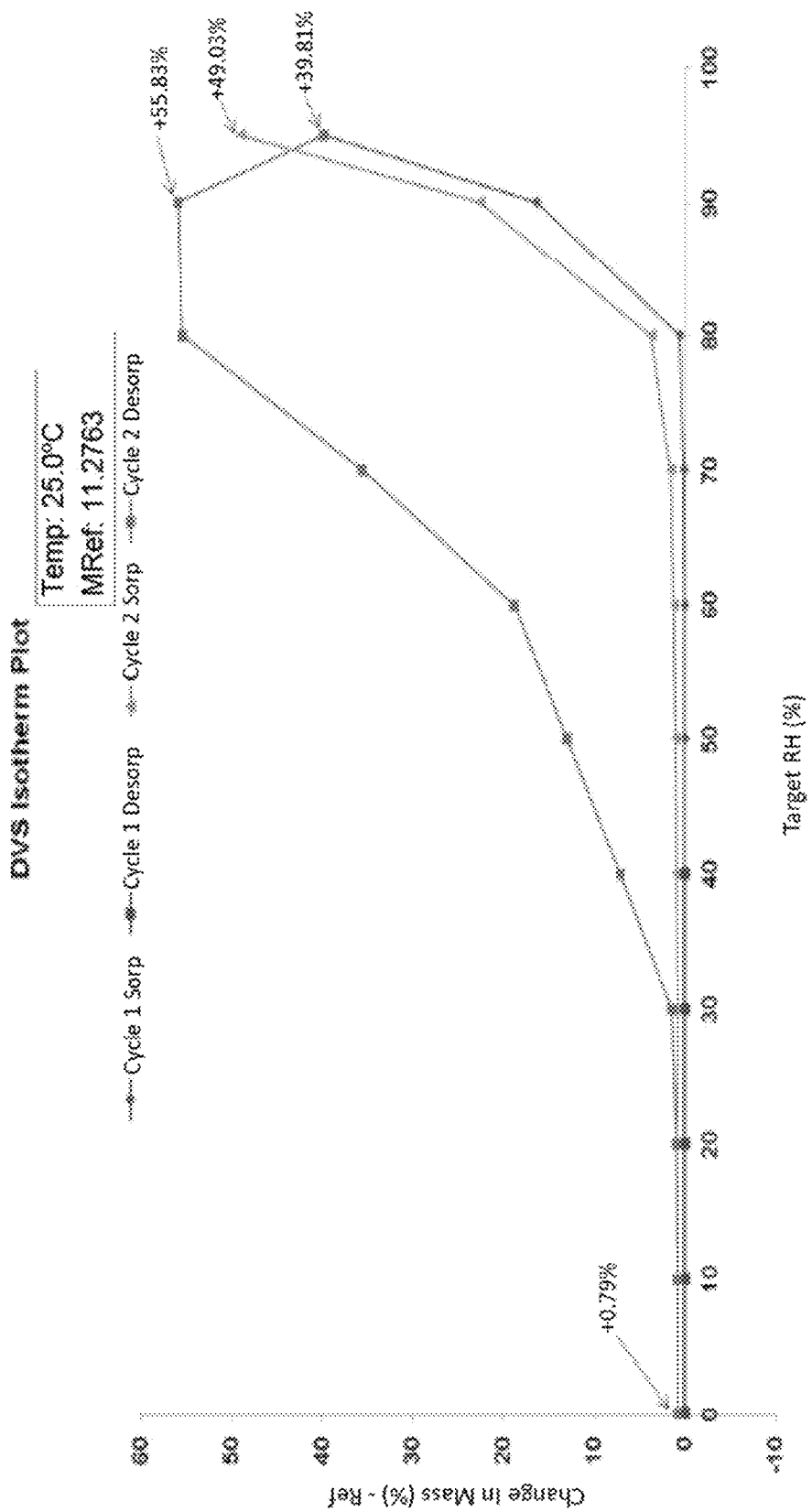
FIGS. 11a and 11b show the change in mass with respect to relative humidity for DVS analysis of Example 2 and Reference Example 3 respectively.
Figure 11B:
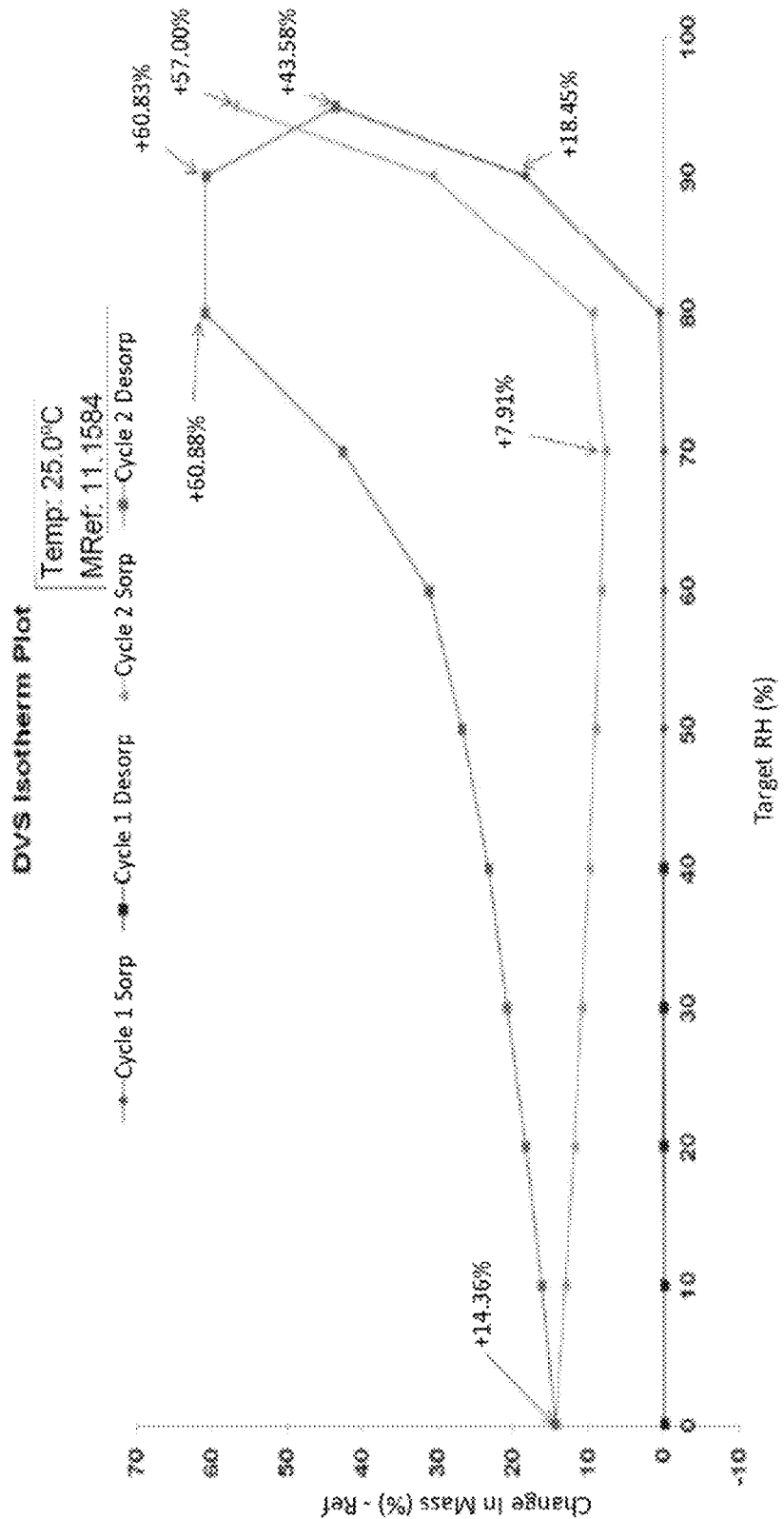

DVS Isotherm plots are provided in FIGS. 11a (Example 2) and 11b (Ref Example 3). The DVS analyses performed on these two samples show a significant weight gain at high relative humidity values (90% RH and above):
at least +55.8% for Example 2
at least +60.8% for Ref Example 3

The desorption stages exhibit different behaviours for the two solids. Example 2 almost reaches its reference weight on the second desorption stage. For Ref Example 3 the weight is still +14.4% higher than the reference weight at the end of the second desorption stage (still +7.9% higher for the minimum value reached). It is worth noting that for the latter the time limit criterion was reached on these steps (the weight of the sample is therefore not stabilized).

Example 5: Heckel Test

The aim of the Heckel test is to compress a test material under controlled conditions to derive the yield pressure of the bulk material. A known weight of material is compressed within a 10 mm diameter die with flat faced punches moving at a set speed. The force on the punch is accurately measured at frequent intervals whilst the displacement of the punches is used to calculate the volume of the powder. The yield pressure is calculated at slow and fast punch speeds to assess the time dependant component to deformation of the material. Samples produced according to Example 2 and Reference Example 3 were subjected to the Heckel test.

Methodology

Determination of True Density by Helium Pychnometry.
Equipment used: Micromeritics AccuPyc 111340
Test Parameters:
Cup size 3.5 cm3
Number of Purges 5
Purge pressure 19.5 psig
Number of runs 10
Run fill pressure 19.5 psig
Equilibration rate 0.02 psig
Run Precision Yes
Percentage full scale 0.05%
Testing was performed in duplicate. (Assuming target <2% variability achieved).

Compression

A known weight of pure drug is compacted to theoretical zero porosity using 10 mm diameter flat faced punches. The Compaction Simulator was used under the following conditions:
Tooling: 10 mm round flat faced
Profile: V shaped profile
Punch speed—Slow 0.1 mm/s
Punch speed—Fast 300 mm/s
Lubrication of die: Yes with Mg stearate in acetone
Number of repeats: 3
Elasticity correction: Yes During compression the location of the punch tips are accurately determined and the force measured by load cells producing a record of the primary compression parameters. Temperature and humidity were monitored at intervals during the test.

The data were analysed by the Compaction Analysis software programme to generate values for yield pressure (Py) using the Heckel equation:

$$\ln\frac{1}{1-D} = kP + A$$

where D=the relative density of the compact
P=Pressure applied
K=Gradient of the line in the linear region
[Reference: R. W. Heckel. Trans. Metall. Soc. AIME 221 (1961)1001-1008]

Strain Rate Sensitivity (SRS)

For some materials, the deformation characteristics change with rate of applied force. This can be estimated by calculating the Strain Rate Sensitivity. The yield pressure at high speed compression is compared to that at slow speed using the following equation:

$$\% \, SRS = \frac{Py\,\text{Fast} - Py\,\text{Slow}}{Py\,\text{Slow}} \times 100$$

[Reference: R. J. Roberts and R. C. Roe, Chem. Eng. Sci. 42(1987) p903].

Results
True Density

TABLE 8

| Run | Ref Example 3 | Example 2 |
|---|---|---|
| Run 1 | 1.3523 g/cm$^3$ | 1.3693 g/cm$^3$ |
| Run 2 | 1.3431 g/cm$^3$ | 1.3973 g/cm$^3$* |
| Run 3 |  | 1.3678 g/cm$^3$ |
| MEAN | 1.3477 g/cm$^3$ | 1.3686 g/cm$^3$ |
|  | (SD 0.013) | (SD 0.002) |

*Variation between runs 1&2 exceeds 2%. 3$^{rd}$ run performed. Data from run 2 assumed an outlier and not used in the mean calculation.

TABLE 9

Compaction Results: Ref Example 3

| Slow speed 0.1 mm/s | Run 1 | Run 2 | Run 3 |
|---|---|---|---|
| Yield Pressure (Mpa) | 101.529 | 95.501 | 97.474 |
| Range of linear region used in calculation (Mpa) | 25-150 | 25-150 | 25-150 |
| Peak Force of Upper punch (kN) | 20.830 | 18.543 | 19.570 |
| Ejection Force (kN) | 0.039 | −0.007 | −0.020 |
| Compact observations: | Good shiny tablet | Good shiny tablet | Good shiny tablet |
| Compact strength (Kiloponds) | 6.41 | 7.45 | 11.17 |

Lab conditions: 21.3° C./52.1% RH

TABLE 10

Compaction Results: Ref Example 3

| Fast Speed 300 mm/s | Run 1 | Run 2 | Run 3 |
|---|---|---|---|
| Yield Pressure (Mpa) | 127.197 | 125.309 | 129.748 |
| Range of linear region used in calculation (Mpa) | 25-150 | 25-150 | 25-150 |
| Peak Force of Upper punch (kN) | 14.644 | 14.752 | 14.617 |
| Ejection Force (kN) | 0.421 | 0.327 | 0.381 |
| Compact observations: | Good but blistering on upper surface and chipping at edges | Good but blistering on upper surface and chipping at edges | Good but blistering on upper surface and chipping at edges |
| Compact strength (Kiloponds) | 6.59 | 4.27 | 4.75 |

Lab conditions: 21.6° C./50.0% RH

TABLE 11

Summary of results and observations

| Property of Batch | Ref Example 3 |
|---|---|
| Yield pressure Slow (0.1 mm/s) | 98.17 Mpa (±3.07) |
| Yield pressure fast (300 mm/s) | 127.42 Mpa (±2.23) |
| Strain rate sensitivity | 29.8% |

TABLE 12

Compaction Results: Example 2

| Slow speed 0.1 mm/s | Run 1 | Run 2 | Run 3 | Run 4 |
|---|---|---|---|---|
| Yield Pressure (Mpa) | 106.465 | 117.516 | 118.116 | 115.227 |
| Range of linear region used in calculation (Mpa) | 25-150 | 25-150 | 25-150 | 25-150 |
| Peak Force of Upper punch (kN) | 20.211 | 24.088 | 24.175 | 23.906 |
| Ejection Force (kN) | 0.044 | 0.053 | 0.080 | 0.060 |
| Compact observations: | Good shiny tablet | Good shiny tablet | Good shiny tablet | Good shiny tablet |
| Compact strength (Kiloponds) | 12.07 | 7.52 | 9.64 | 9.19 |

Lab conditions: 21.7° C./51.1% RH

TABLE 13

Compaction Results: Example 2

| Fast Speed 300 mm/s | Run 1 | Run 2 | Run 3 |
|---|---|---|---|
| Yield Pressure (Mpa) | 129.865 | 129.108 | 129.861 |
| Range of linear region used in calculation (Mpa) | 25-150 | 25-150 | 25-150 |
| Peak Force of Upper punch (kN) | 14.566 | 14.542 | 14.717 |
| Ejection Force (kN) | 0.441 | 0.456 | 0.417 |
| Compact observations: | Good but blistering to upper surface and lower punch sticking | Good shiny tablet. Sticking and chipping to lower edge. | Good shiny tablet. Sticking and chipping to lower edge. |
| Compact strength (Kiloponds) | 9.83 | 11.58 | 8.88 |

Lab conditions: 21.7° C./51.2% RH

TABLE 14

Summary of results and observations

| Property of Batch | Example 2 |
|---|---|
| Yield pressure Slow (0.1 mm/s) | 114.33 Mpa (±5.39) |
| Yield pressure fast (300 mm/s) | 129.61 Mpa (±0.44) |
| Strain rate sensitivity | 13.4% |

Figure 6:
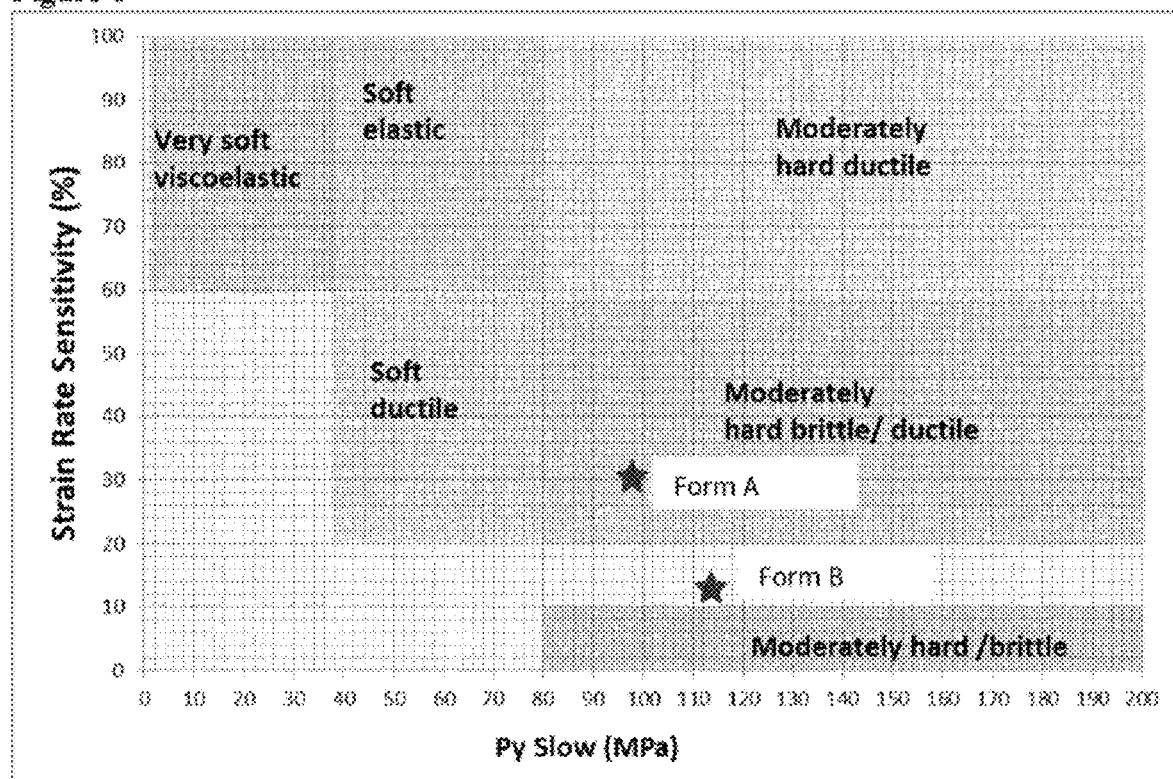
FIG. 6 depicts a Heckel plot of TETA.4HCl Form A and TETA.4HCl Form B.

The Heckel test is a measure of the deformation of a formed tablet. The compact strength is an indication of how the dwell time affects bonding of the compact. It was found that Reference Example 2 compacts produced at slow speed had moderate tensile strength (6-11 kiloponds). At fast speed, strength reduced to about 4-6 kiloponds. Example 3 on the other hand showed strengths of 7-12 kiloponds at slow speed, but 9-11 kiloponds at fast speed, showing that Example 3 has a greater tensile strength of compacted product at fast compaction fates. FIG. 6 shows the strain rate sensitivity of Example 2 and Reference Example 3 at different production speeds.

Example 6: Aging of Tablets

TETA.4HCl obtained in accordance with Reference Example 3 was compressed to form a tablet. An image of the tablet is provided in FIG. 7a. The tablet was aged for six months at 40° C. and 75% humidity. After aging, the tablet was observed to have a number of discoloured patches. An image of the aged tablet is provided in FIG. 7b.

Figure 7C:
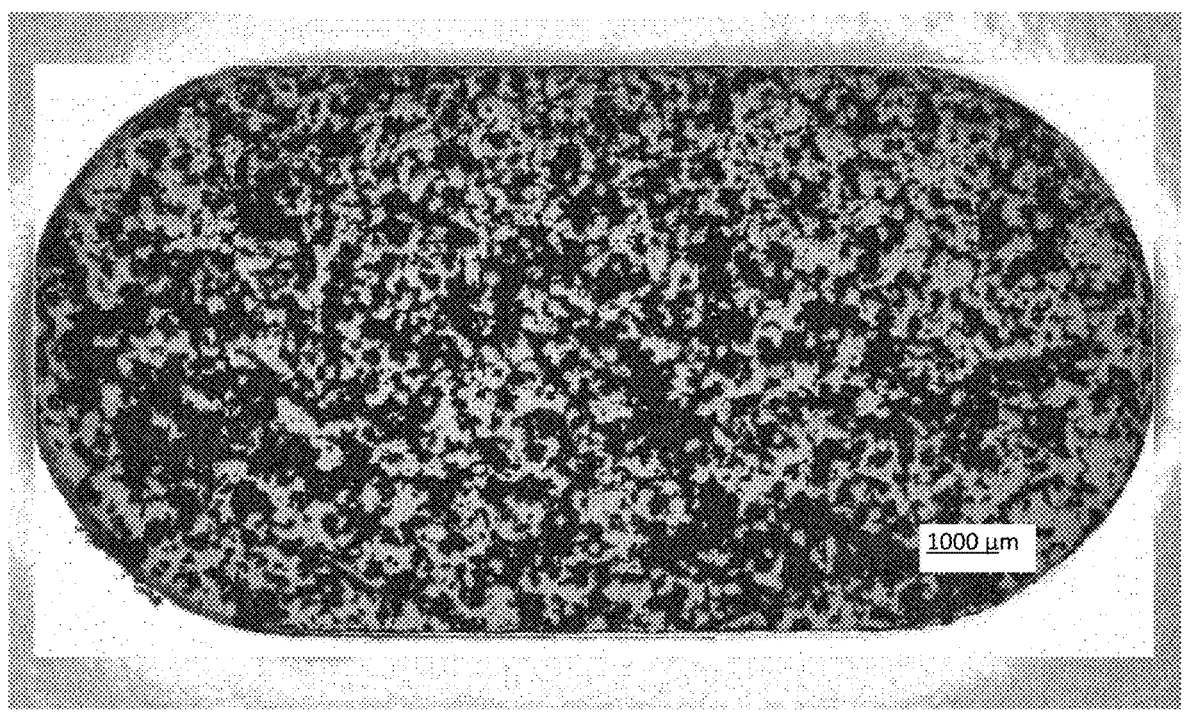
FIG. 7c shows a Raman analysis of the aged tablet, with the darkened regions corresponding to the location of TETA.4HCl Form A in the tablet.

The tablet was analysed by Raman spectroscopy under the same conditions as are set out in Example 4 above and the results compared with the Raman spectra for Form A and Form B TETA.4HC. FIG. 7c shows in darkened regions the areas of the tablet which show the presence of TETA.4HCl Form A. As is apparent from a comparison of FIGS. 7b and c, the areas of TETA.4HCl Form A correlate to the location of the discoloured regions on the tablet surface.

Minute amounts of TETA.4HCl Form B were detected in the tablet which may have formed under compression of TETA.4HCl to form a tablet. The areas of TETA.4HCl Form B do not correlate to the discoloured regions observed in the aged tablet.

Example 7: Crystallisation Process

Crystallization tests for the preparation of Form B were carried out at 20° C. Starting solutions were prepared in a mixture of ethanol/water at (25:75) and the addition of ethanol was performed until a (75:25) ratio was reached. First tests were carried out by manually adding ethanol. Additional tests were then performed using a syringe pump, for an addition at a slow and controlled rate.

Manual Addition (Dropwise)

In these tests, the addition was carried out manually using a micropipette. A solution of TETA.4HCl in a (25:75) ethanol/water mixture was placed under stirring and thermostated at 20° C. The amount of TETA.4HCl starting material is set out in Table 15.

Anti-solvent (ethanol) was added dropwise, at a regular interval. Two "rates" of addition were tested. After the addition of the anti-solvent, the solid phase was sampled and analysed by X-ray diffraction in order to determine the nature of the solid phases. Conditions of X-ray diffraction were as set out in Example 4. The last test was performed with seeds of Form B present at the beginning of the addition, and at a slower rate of addition (PE1716E007-L-5). This test leads to a solid phase with no signal of Form A observed on the diffractogram.

Figure 9A:
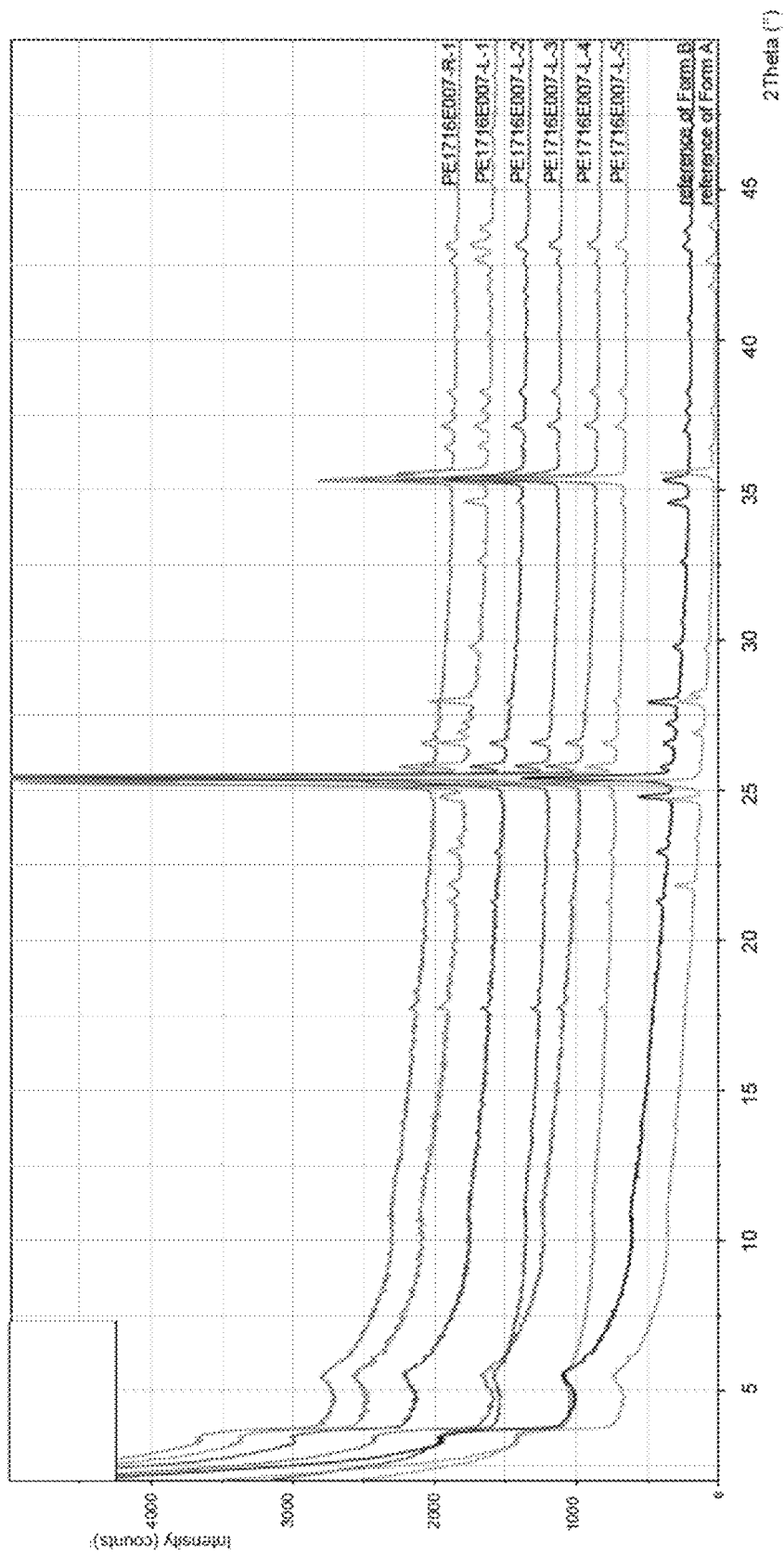
FIG. 9a shows X-ray Powder diffraction analyses on the samples of Example 7 after manual addition of ethanol at different speeds, and comparison with the reference patterns of Form A and Form B.
Figure 9B:
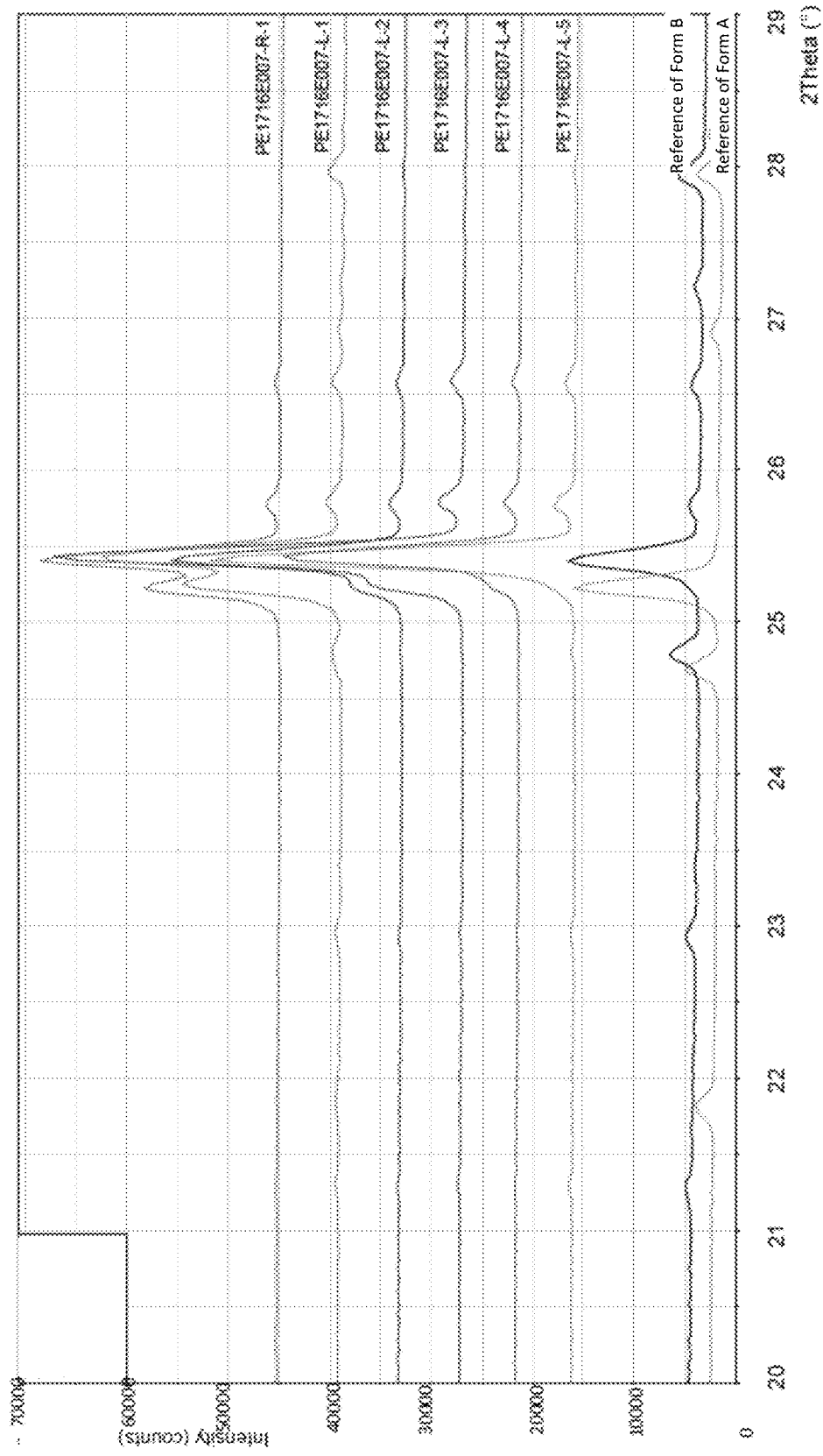
FIG. 9b shows magnification of FIG. 9a on 2θ=20-29°.
Figure 9C:
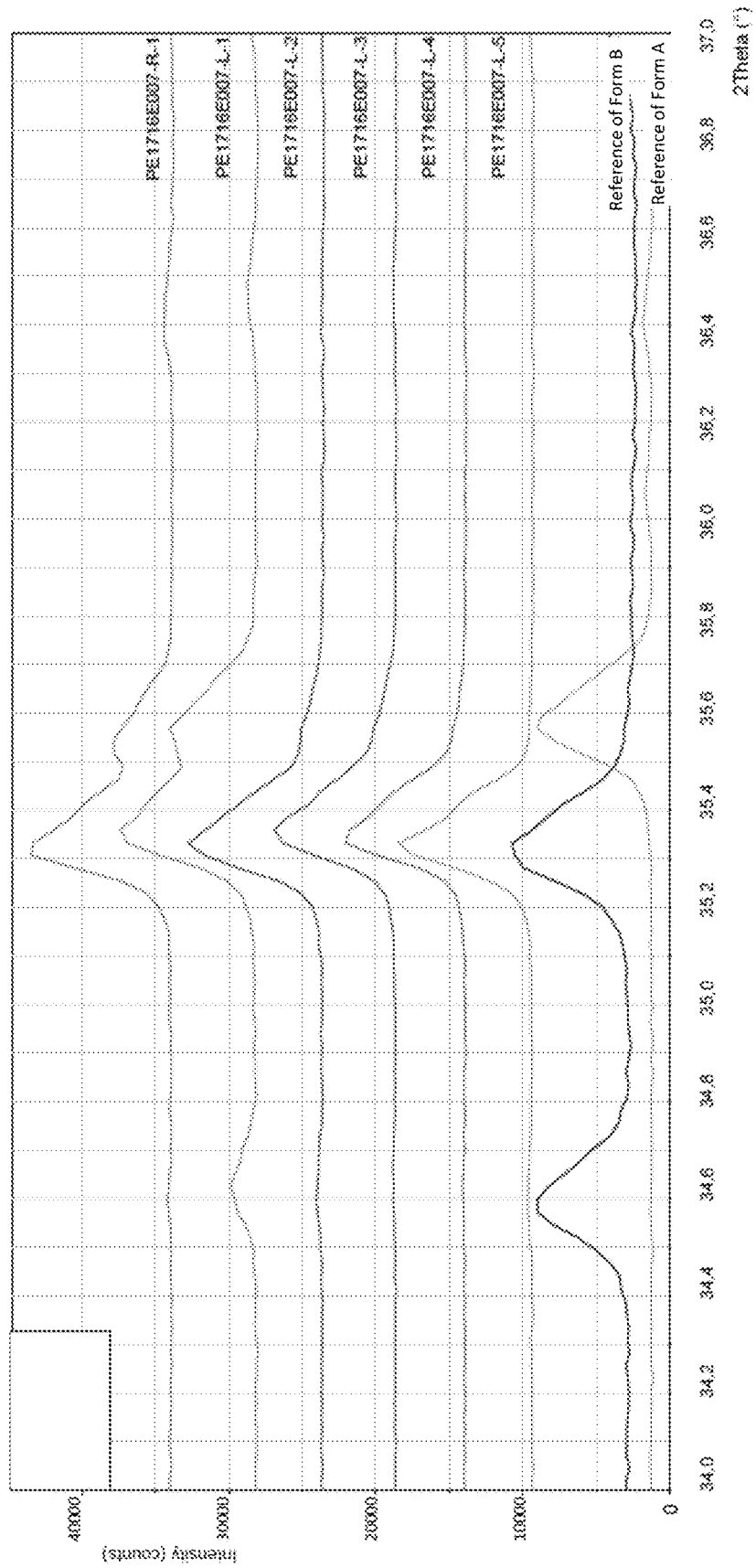
FIG. 9c shows magnification of FIG. 9a on 2θ=34-37°.

The results are set out in Table 15 and the diffractograms obtained after the analysis of the solid phases in suspension at the end of the ethanol addition are presented in FIGS. 9a, b and c. FIGS. 9a-c show XRPD diffractograms for, beginning at the lowest line:

Reference of Form A (Bottom Line in FIGS. 9a-c)
Reference of Form B
PE1716E007-L-5
PE1716E007-L-4
PE1716E007-L-3
PE1716E007-L-2
PE1716E007-L-1
PE1716E007-R-1 (top line in FIGS. 9a-c)

TABLE 15

Table 15. Results of the crystallization tests by manual addition.

| Test reference | m starting material (mg) | m solvent mixture (mg) | Initial Concentr. (mg/mg solution) | Seeds (mg) | Solvent added (µL) | Solvent added (mg) | Total time | Final Concentr. (mg/mg solution) | XRD Profile XRD reference |
|---|---|---|---|---|---|---|---|---|---|
| PE1716E007-R-1 | 192.71 | 384.45 | 0.334 | No | 816 | 643.8 | 2 s | 0.158 | Form B + Form A |
| PE1716E007-L-1 | 190.28 | 387.53 | 0.329 | No | 816 | 643.8 | 1 min | 0.156 | Form B + Form A |
| PE1716E007-L-2 | 702.48 | 1445.64 | 0.327 | No | 3000 | 2367 | 1 min | 0.156 | Form B + Form A |
| PE1716E007-L-3 | 703.91 | 1445.90 | 0.327 | No | 3000 | 2367 | 1 min | 0.156 | Form B + Form A |
| PE1716E007-L-4 | 748.33 | 1462.15 | 0.339 | No | 3000 | 2367 | 5 min | 0.163 | Form B + Form A (weak) |
| PE1716E007-L-5 | 750 | 1452.53 | 0.341 | 2.72 | 3000 | 2367 | 32 min | 0.164 | Form B |

Programmed Addition (Continuous)

In this series of tests, the addition of the antisolvent was driven by syringe pump. This allowed a continuous addition at a very low rate. The same protocol as above was used: a solution of the starting material was prepared, close to saturation, in a 25:75 ethanol/water mixture as set out in Table 16. The solution was then saturated with Form B until a solid phase remained in suspension: this ensures the presence of seeds of Form B at the beginning of anti-solvent addition.

Two rates of addition were tested: 0.05 mL/min and 0.1 mL/min (for 750 mg starting material in solution). Ethanol was added at these selected rates until a 75:25 ethanol/water ratio was obtained. Two additional tests were performed with an addition up to 82:18 which corresponds to a concentration of about 12.5%, and up to 87.5/12.5 ratio, which corresponds to a concentration of about 9% (starting material/total weight).

The X-ray diffraction analyses were performed using the conditions set out in Example 4. The results are shown in Table 16 below and the diffractograms obtained after the analysis of the solid phases in suspension at the end of the ethanol addition are presented in FIGS. 10a to 10c. These show diffraction profiles with no signal of Form A observed for the two tests with a final ethanol/water ration at 75:25 and the test at 87.5:12.5. A small shoulder on the left of the peak at 2θ=25.4° (corresponding to Form A) for the test at 82:18.

Figure 10A:
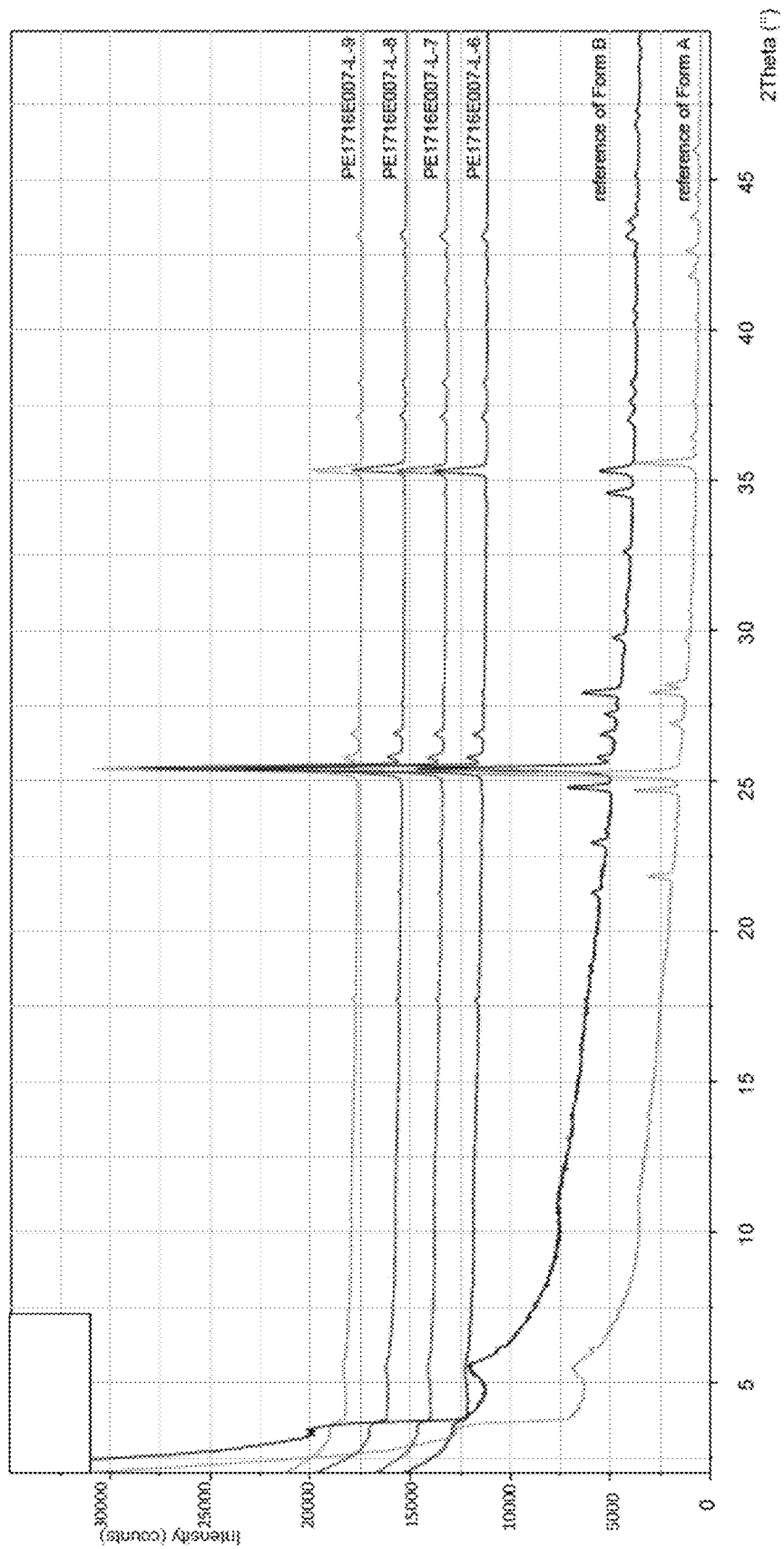
FIG. 10a shows X-ray Powder diffraction analyses on the samples of Example 7 after programmed addition of ethanol, and comparison with the reference patterns of Form A and Form B.
Figure 10B:
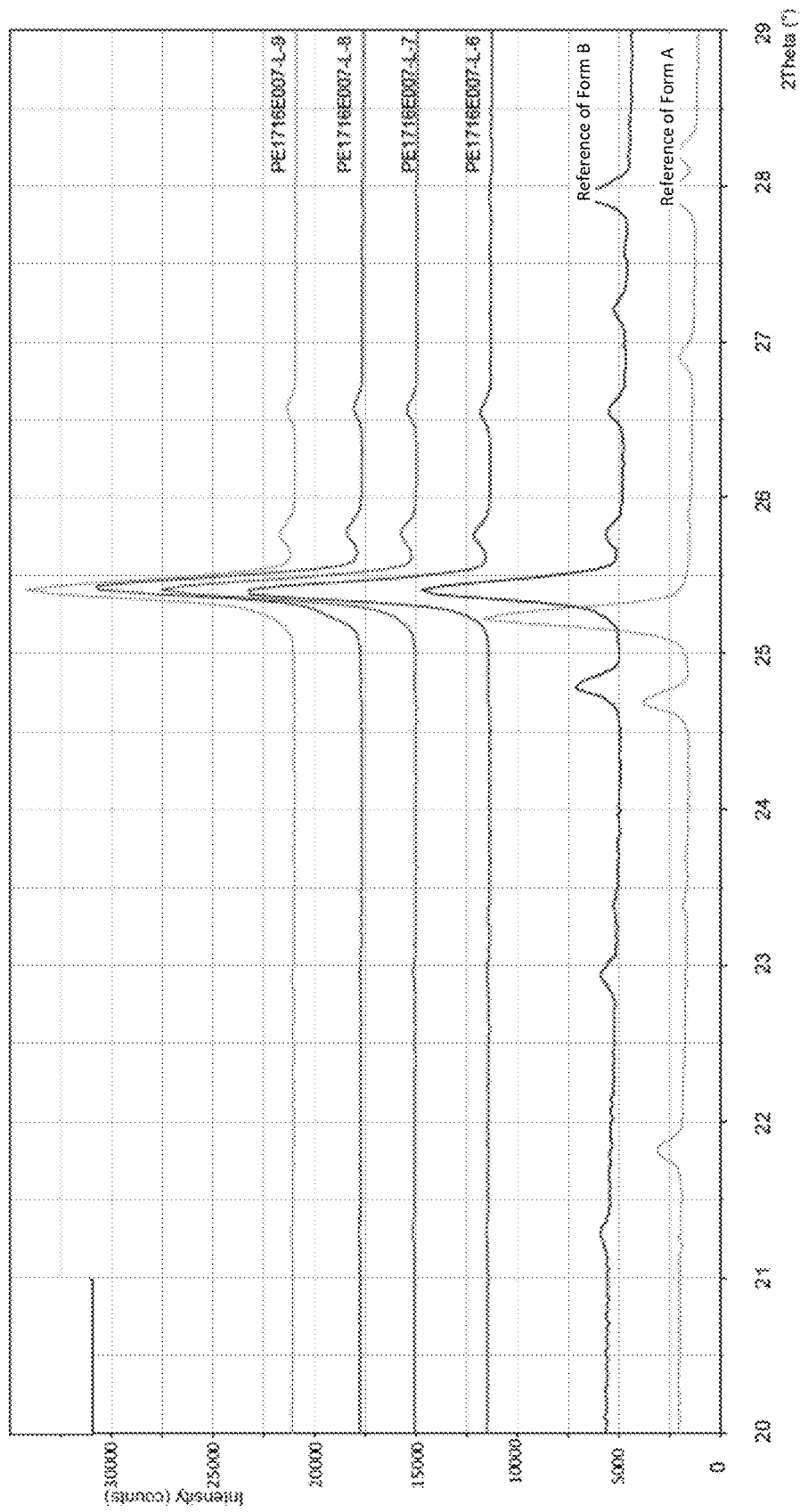
FIG. 10b shows magnification of FIG. 10a on 2θ=20-29°.
Figure 10C:
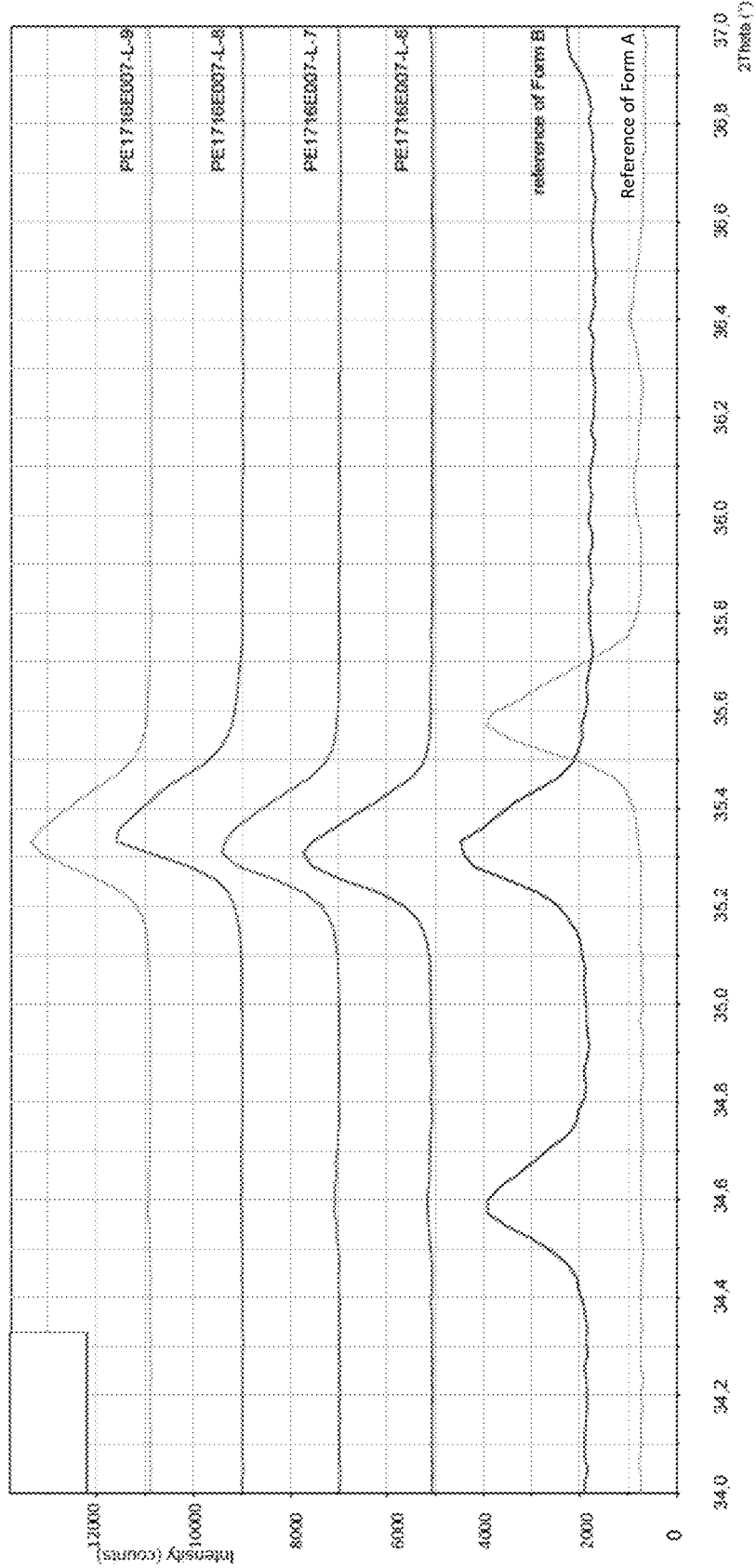
FIG. 10c shows magnification of FIG. 10a on 2θ=34-37°.

FIGS. 10a-c show XRPD diffractograms for, beginning at the lowest line:
Reference of Form A (bottom line in FIGS. 10a-c)
Reference of Form B
PE1716E007-L-6
PE1716E007-L-7
PE1716E007-L-8
PE1716E007-L-9 (top line in FIGS. 10a-c)

TABLE 16

Results of the crystallization tests by programmed addition

| Test reference | m starting material (mg) | m solvent mixture (mg) | Initial Concentr. (mg/mg solution) | Seeds (mg) | Solvent added (μL) | Solvent added (mg) | Add. rate (mL/min) | Final Concentr. (mg/mg solution) | XRD Profile XRD reference |
|---|---|---|---|---|---|---|---|---|---|
| E007-L-6 | 750.24 | 1449.99 | 0.341 | 2.93 | 3000 | 2367.0 | 0.05 | 0.164 | Form B PE1716X048 |
| E007-L-7 | 749.20 | 1448.69 | 0.341 | 5.29 | 3000 | 2367.0 | 0.1 | 0.164 | Form B PE1716X049 |
| E007-L-8 | 750.57 | 1445.90 | 0.342 | 2.90 | 4844 | 3821.9 | 0.1 | 0.125 | Form B + Form A (weak) PE1716X050 |
| E007-L-9 | 749.22 | 1445.08 | 0.341 | 2.98 | 7783 | 6140.8 | 0.1 | 0.090 | Form B PE1716X051 | isolated. The crude triethylenetetramine tetrahydrochloride (Crude TETA 4HCl) is obtained by reaction of triethylenetetramine hydrate (TETA hydrate) with aqueous hydrochloric acid in ethanol (Step II). The crude triethylenetetramine tetrahydrochloride (Crude TETA 4HCl) is recrystallised from a mixture of purified water and ethanol. The crude triethylenetetramine tetrahydrochloride (Crude TETA 4HCl) is further purified by recrystallisation from a mixture of purified water and ethanol in the presence of Form B seeds to give triethylenetetramine tetrahydrochloride (TETA 4HCl) (Step III).

The method produces a batch size of 110-130 kg TETA 4HCl, from 125 kg of TETA. The overall yield for the synthesis is approximately 50% including two recrystallisations of crude TETA 4HCl. The recrystallization to produce Form B crystals is carried out as summarised in the flow charts of FIGS. 1a, 1b and 2, but with the addition of a further recrystallization of the crude TETA.4HCl at the end of Step II (FIG. 1b) and before Step III (FIG. 2). The process can be described as follows:

Once inertisation of the installations has been performed, all manipulations are performed under nitrogen flow.

Step I: Manufacture of Triethylenetetramine Hydrate (TETA Hydrate)

Triethylenetetramine (nominal quantity 125 kg) is charged into a reactor followed by TBME (185±5 kg).

Example 8: Crystallisation Process

An overview of the synthesis of triethylenetetramine (trientine) tetrahydrochloride (TETA 4HCl) is shown in the scheme below.

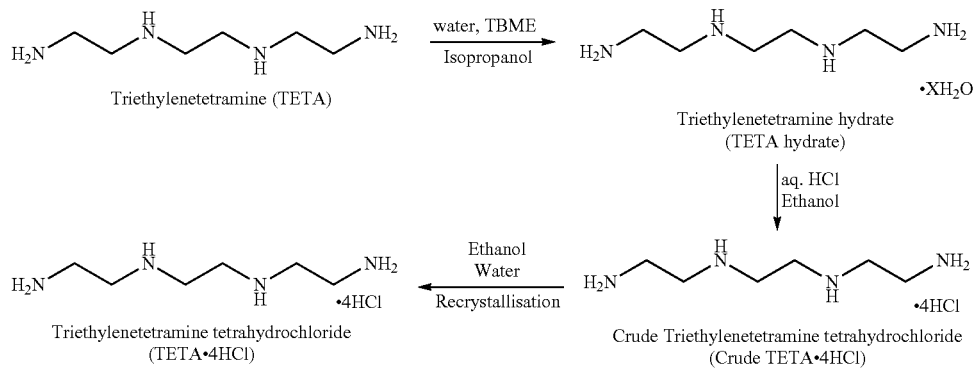

In Step I. triethylenetetramine (TETA) is converted to the corresponding triethylenetetramine hydrate (TETA hydrate) by stirring in the presence of water and TBME. Isopropanol is added as an anti-solvent and if required, seeded with TETA hydrate. The TETA hydrate is crystallised, filtered and Water (ca 28 kg) is added with stirring over ≥15 minutes whilst maintaining the temperature at ≤30° C. The solution is seeded with triethylenetetramine hydrate (ca. 0.1 kg) whilst stirring at 25-35° C., if required, to promote crystallisation.

Isopropanol (64±1 kg) is added at 25-35° C.

The suspension is heated at 30-40° C. for ≥15 minutes, followed by a slow cooling over ≥90 minutes to 15-25° C.

The suspension is cooled to −5 to 5° C. and is stirred for ≥30 minutes

The product is filtered and centrifuged. Then, a sample is taken for analysis (GC Assay) and determination of impurities.

If the sample is sufficiently pure, the wet TETA hydrate is filled in the dryer and dried at ≤25° C. until it meets the requirements set out in the next step.

The dried product is analysed for purity by GC, appearance, residual water by KF, identity by FTIR, sulphated ash and residual solvents by GC.

Step II: Manufacture of Crude Triethylenetetramine Tetrahydrochloride (Crude TETA.4HCl)

Triethylenetetramine hydrate (TETA hydrate) is dissolved in water (85±1 kg) and acidified with concentrated aqueous hydrochloric acid (200±5 kg) charged over ≥1 h at ≤40° C. The pH value is checked (target pH=1.0) and concentrated aqueous hydrochloric acid is added until pH≤1.0 is met.

The reaction mixture is cooled to 15-25° C. and stirred for ≥10 minutes.

The solution is treated with ethanol (672±5 kg) which is charged over ≥1.5 h, maintaining the temperature at ≤30° C.

The suspension is cooled to −5 to 5° C. and stirred for ≥30 minutes.

The product is filtered and the solid washed successively with ethanol (1×20 kg, then 3×25 kg).

Crude triethylenetetramine tetrahydrochloride (crude TETA.4HC) is dissolved in water (340±10 kg).

The solution is treated with ethanol (909±10 kg) which is charged over ≥1.5 h, maintaining the temperature at ≤30° C.

The suspension is cooled to −5 to 5° C. and stirred for ≥30 minutes.

The product is filtered and the solid washed successively with ethanol (1×14 kg, then 3×15 kg).

Step III: Manufacture of Triethylenetetramine Tetrahydrochloride (TETA.4HCl)

Crude triethylenetetramine tetrahydrochloride (crude TETA.4HC) is dissolved in water (340±10 kg).

The solution is treated with ethanol (909±15 kg) which is charged over ≥1.5 h, maintaining the temperature at 7-13° C.

The solution is seeded with TETA.4HCl (2 wt %) during the ethanol addition.

The suspension is stirred for ≥5 hours, then cooled to −5° C. and stirred for ≥30 minutes.

The product is filtered and the solid washed successively with ethanol (1×14 kg, then 3×15 kg).

A sample of the product is analysed for purity by GC.

The product is dried at ≤40° C. and if the control parameter for loss-on-drying is met, the product is milled.

The milled drug substance is transferred under nitrogen in double food quality polyethylene bag and then placed in an aluminium bag and sealed. The aluminium bag is inserted in a HDPE drum.

Reprocessing

TETA 4HCl obtained after recrystallisation is tested for impurities by GC. If levels of impurities are too high, Step III can be repeated.

The invention claimed is:

1. A crystalline form of triethylenetetramine tetrahydrochloride Form B having at least one of the following characteristics:
   (i) an XRPD pattern having at least two peaks selected from the peaks at 22.9, 25.4, 25.8, 26.6, 34.6 and 35.3±0.1°2θ; and
   (ii) a Raman spectrum having at least two peaks selected from the peaks at a Raman shift of 943, 1173, 1527 and 1612±5 cm$^{-1}$;
   wherein the crystalline form contains no more than 10 wt % of triethylenetetramine tetrahydrochloride Form A having an XRPD pattern having peaks at 25.2 and 35.7±0.1°2θ; and
   XRPD pattern peaks are as measured using a wavelength of 1.5418 Å.

2. The crystalline form according to claim 1, having an XRPD pattern having peaks at 25.4, 34.6 and 35.3±0.1°2θ.

3. The crystalline form according to claim 1, which contains at least 95 wt % of triethylenetetramine tetrahydrochloride Form B having:
   (i) an XRPD pattern as defined in claim 1; and/or
   (ii) a Raman spectrum having at least two peaks selected from the peaks at a Raman shift of 943, 1173, 1527 and 1612±5 cm$^{-1}$.

4. A pharmaceutical composition comprising the crystalline form according to claim 1 and a pharmaceutically acceptable carrier or diluent.

5. The pharmaceutical composition according to claim 4, which contains no more than 5 wt % triethylenetetramine tetrahydrochloride Form A having an XRPD pattern having peaks at 25.2 and 35.7±0.1°2θ.

6. The pharmaceutical composition according to claim 5, which contains no more than 2 wt % triethylenetetramine tetrahydrochloride Form A having an XRPD pattern having peaks at 25.2 and 35.7±0.1°2θ.

7. The pharmaceutical composition according to claim 5 which contains no more than 1 wt % triethylenetetramine tetrahydrochloride Form A having an XRPD pattern having peaks at 25.2 and 35.7±0.1°2θ.

8. A solid oral dosage composition comprising the crystalline form according to claim 1 and a pharmaceutically acceptable carrier.

9. A solid oral dosage composition comprising the crystalline form according to claim 2 and a pharmaceutically acceptable carrier.

10. A solid oral dosage composition comprising the crystalline form according to claim 3 and a pharmaceutically acceptable carrier.

* * * * *